US008560334B2

(12) United States Patent
Lähteenmäki

(10) Patent No.: US 8,560,334 B2
(45) Date of Patent: Oct. 15, 2013

(54) METHOD AND ARRANGEMENT FOR ARRANGING AN INFORMATION SERVICE TO DETERMINE NUTRITION AND/OR MEDICATION

(76) Inventor: Pertti Lähteenmäki, Helsinki (FI)

( * ) Notice: Subject to any disclaimer, the term of this patent is extended or adjusted under 35 U.S.C. 154(b) by 1918 days.

(21) Appl. No.: 10/328,044

(22) Filed: Dec. 26, 2002

(65) Prior Publication Data

US 2003/0182160 A1     Sep. 25, 2003

(30) Foreign Application Priority Data

Dec. 28, 2001    (FI) ...................................... 20012593

(51) Int. Cl.
G06Q 50/00    (2012.01)
G06Q 10/00    (2012.01)

(52) U.S. Cl.
USPC .................................................. 705/2; 705/3

(58) Field of Classification Search
USPC ............................................................ 705/2
See application file for complete search history.

(56) References Cited

U.S. PATENT DOCUMENTS

| | | | |
|---|---|---|---|
| 5,233,520 A | 8/1993 | Kretsch et al. | |
| 5,412,564 A | 5/1995 | Ecer | |
| 5,836,312 A * | 11/1998 | Moore | 128/897 |
| 5,985,559 A | 11/1999 | Brown | |
| 6,000,828 A | 12/1999 | Leet | |
| 6,024,281 A | 2/2000 | Shepley | |
| 6,038,546 A | 3/2000 | Ferro | |
| 6,056,690 A * | 5/2000 | Roberts | 600/300 |
| 6,081,786 A * | 6/2000 | Barry et al. | 705/3 |
| 6,188,988 B1 | 2/2001 | Barry et al. | |
| 6,272,472 B1 * | 8/2001 | Danneels et al. | 705/27 |
| 6,283,914 B1 | 9/2001 | Mansfield et al. | |
| 6,678,669 B2 * | 1/2004 | Lapointe et al. | 706/15 |
| 2001/0034023 A1 | 10/2001 | Stanton, Jr. et al. | |
| 2002/0082869 A1 * | 6/2002 | Anderson | 705/3 |

FOREIGN PATENT DOCUMENTS

| | | |
|---|---|---|
| CN | 1312468 A | 9/2001 |
| DE | 10035702 A1 * | 2/2002 |
| EP | 0 427 875 A1 | 5/1991 |
| EP | 1 176 539 A1 | 1/2002 |
| JP | 07271857 | 10/1995 |
| JP | 2002358362 | 12/2002 |

(Continued)

OTHER PUBLICATIONS

Honkela, Timo, Kaski, Samuel, Lagus, Krista, and Kohonen, Teuvo, "Newsgroup Exploration with WEBSOM Method and Browsing Interface", Jan. 1996, Helsinki University of Technology, Report A32, pp. 4, 8, and 11-12.*

(Continued)

Primary Examiner — Tran Nguyen
(74) Attorney, Agent, or Firm — Young & Thompson

(57) ABSTRACT

An arrangement for arranging an information service is configured to manage at least one probability weighting coefficient of an influence of at least one gene being in a functional state to at least one health property with a certain probability, and at least one probability weighting coefficient to at least one nutrient and/or medical substance influencing at least one health property in a healing or harmful manner with a certain probability. In addition, the arrangement is configured to form information describing the suitability of the nutrient and/or medical substance for the user with the help of the probability weighting coefficients.

14 Claims, 6 Drawing Sheets

(56) References Cited

FOREIGN PATENT DOCUMENTS

| WO | 00/51053 | | 8/2000 |
|---|---|---|---|
| WO | 01/95230 | A2 | 12/2001 |
| WO | 02/37398 | A2 | 5/2002 |

OTHER PUBLICATIONS

Ruzicka, Atopic Eczema Between Rationality and Irrationality, Arch Dermatol. 1998;134:1462-1469.*

Ellwood, Finding Foods That Agree With Our Genes, Agricultural Research/Mar. 2001.*

Robert Kowalski, "Predicate Logic as Programming Language," Proceedings of Information Processing IP, 1974, pp. 569-574.

Johan de Kleer, "An Assumption-Based TMS," Journal of Artificial Intelligence, V. 28, 1986, pp. 127-162.

A.P. Dempster, "Upper and Lower Probabilities Induced by a Multivalued Mapping," Anneals of Mathematical Statistics, V. 38, pp. 325-339.

G. Shafer, "The Mathematical Theory of Evidence," 1976, pp. 34-273.

* cited by examiner

| | | | | | 500 |
|---|---|---|---|---|---|
| 502 | 504 | 506 | 508 | 510 | |

Food product | Nutrient | Amount | Manufacturing method | Time
--- | --- | --- | --- | ---
Meat > | energy | 700 kJ | Deep fried | 28.11  7:50
Fish > | protein | 18 g | Fried | 28.11  11:00
Root crops > | carbonhydr | 200 g | Boiled | 27.11  21.30
Vegetables > | Fat | 7 g | Fresh | 27.11  21.30
Fruits > | Salt | 3 g | | 27.11  21.45
Milk products | Sugar | 1 g | | 27.11  21.45

****** 511

524 — Add | Delete | Change | 522 | Send / Cancel — 520

| | | | | | 550 |
|---|---|---|---|---|---|
| 552 561 | 554 | 556 | 558 | 560 | |

Performance | Duration | Amount | Level of difficulty | Time
--- | --- | --- | --- | ---
Walking | 1h 30 m | 7200 m | ⦿ Demanding | 28.11  7:50
Jogging | | | ○ Average | 28.11  11:00
Running | | 572 | ○ Easy | 27.11  21.30
Cycling | | | | 27.11  21.30
Swimming | | | | 27.11  21.45
Gym | | | | 27.11  21.45
Golf | | | 574 ****** | Send / Cancel — 570

Add | Delete | Change | | 568

METHOD AND ARRANGEMENT FOR ARRANGING AN INFORMATION SERVICE TO DETERMINE NUTRITION AND/OR MEDICATION

BACKGROUND OF THE INVENTION

1. Field of the Invention

The present invention relates to a method and arrangement for arranging an information service to determine nutrition and/or medication. More specifically, the invention relates to the formation of information related to the suitability of nutrients and/or medical substances for different parties and to the transmission of information between different parties and systems.

2. Description of the Related Art

In the past decades, the average life expectancy of human beings has grown considerably because of the advanced medical methods of treatment. At the same time, new diseases and illnesses have come out, such as different kinds of allergies, especially to foodstuffs. In addition, obesity has become common especially in developed countries, in which the daily motion of humans has continuously decreased, for example, due to work performed by humans becoming lighter and due to automation. At the same time, humans' eating habits have changed, for example, as so-called fast-food restaurants have become more common. Although specific special foodstuffs and health foods are now in good supply, nevertheless, the major part of humans eats in an unhealthy or unsuitable way, for example, in relation to the energy consumption, illness or latent illness, and they do not think about the nutrients contained in the nutrition they consume or their effects on their health. The significance of nutrients contained in the nutrition frequently consumed, for example, in the generation and progress of illnesses is not even realised, and staying healthy is considered obvious.

However, the consumed nutrition plays an important role in the generation and progress of almost all illnesses. Especially for persons following a special diet, such as weight-watchers, allergic persons, diabetics, and persons suffering from other illnesses, sportsmen and persons otherwise taking care of their health, the additives and nutrients contained in the nutrition and medicaments, and their amounts and/or proportions are especially important for the optimal result, for staying healthy and/or for preventing the worsening of an illness. However, it has to be noted that also healthy persons should watch the quality, amounts and proportions of nutrients contained in the nutrition they consume in order to stay healthy, fit for work and vital.

However, monitoring the nutrients contained in the consumed nutrition is often considered difficult or laborious, and it is only thought to be relevant mostly for persons following a special diet for one reason or another. In some cases, it may also be difficult for people to monitor the nutrient contents in the consumed food and/or drink or other substances contained in foods, which may, for example, cause illnesses or make allergies worse. For example, people may have difficulties in remembering or generally in knowing all nutrients harmful for them in the foodstuffs, in which case, for example when shopping, it may be difficult to know the suitability of a certain product. Especially, if one thinks of the overall effect of nutrients acquired in one day or even one week, it is almost impossible to find out the suitability, goodness and/or effect of a certain foodstuff in relation to the overall effect of nutrients obtained in one day or one week.

Solutions for informing the user of nutrients contained in the nutrition are previously known, for example, from the publications U.S. Pat. Nos. 6,024,281 and 6,038,546. In the solution of the publication U.S. Pat. No. 6,024,281, personal nutrient information is formed to the user with the help of information fed by the user and identifying the food product and with the help of the user's personal data, using a special nutrient information system. Again, in the solution of the publication U.S. Pat. No. 6,038,546, the portions offered by a restaurant are prepared of one or several standardised food articles or components according to the meal order of the customer, in which case the meal will comprise a standardised or modified amount of food components, and the list of nutrients in the portion can be delivered to the customer.

Different computer programs and data terminal equipment are further known for monitoring the supply of nutrients of a person, for example, during dieting or weight watching. For example, the publication U.S. Pat. No. 5,412,564 discloses a solution, in which the nutrition consumption of a consumer can be monitored and information concerning nutrition consumption can be recorded. The publication U.S. Pat. No. 5,233,520 again discloses a solution for an interactive, computerised measuring apparatus of nutrition, which can be used for measuring the food, nutrients and other food components consumed by a person.

However, arrangements according to the known solutions contain some drawbacks. The solutions are typically intended mainly for monitoring certain nutrients in the foodstuffs, and they have been realised mainly by directly comparing, for example, the nutrients contained in a certain food or component with information fed by the user, such as identifier information of substances causing allergy, in which case, if the mentioned food or component contains a nutrient unsuitable for the particular user, the system according to the solution informs the user of this. However, the arrangements according to the solutions do not take into account, for example, the user's genetic genotype and the special requirements caused by this to the nutrient contents, additives, nutrients and/or their proportions in the user's diet.

Further, the systems according to known solutions are clumsy, due to the inflexibility of their user interfaces. The systems of the known solutions are typically arranged to be used, for example, in connection of special nutrition information systems in a shop, in which the arrangement comprises information on the nutrition content of the products that are sold in the shop in question. In a second known solution, the user can search information on nutrients using his home computer, for example, from a database to be supplied on a CD ROM disc. However, the user interfaces of the known solutions restrict the user's moving, in which case situations may often occur in which it is not possible to unambiguously check the nutrients in a certain foodstuff and/or the suitability of these nutrients for the so-called user. In addition, in the arrangements of the known solutions, it is difficult to control or keep up-to-date the amounts and proportions of all nutrients consumed by the user, due to the place-bound arrangements according to the known solutions.

In the state-of-the-art solutions, it is further difficult for the medical personnel treating the user to monitor the supply of nutrients and/or medicaments consumed by the user. In addition, the state-of-the-art solutions have not presented an effectively working solution, in which doctors, nurses or the user would be offered a possibility to easily change, for example, the list of substances harmful for the user in the nutrition information system. The problem of the state-of-the-art solutions is that the arrangements are rigid and inflexible, for example, in a situation, in which the user suddenly gets allergy, and the database of foods suitable or unsuitable for the user should be updated fast.

SUMMARY OF THE INVENTION

The object of the invention is to create a solution for arranging a nutrition and medication information service so that the said drawbacks of the state-of-the-art technology can be reduced. The invention aims to solve how the user can easily check the suitability of amounts and/or proportions of nutrients contained in a foodstuff and/or medicament, taking into account the user's possible illnesses, special diets, environmental conditions and genotype, and the medical and biological research information available. It is further the object of the invention to create a solution, with which an individualised and optimal nutrition and metabolic condition and a possible medication can be tailored to the user, taking into account the user's genotype, possible illnesses and environmental conditions.

The objects of the invention are achieved so that information obtained about the user's genetic properties, possible illnesses, environmental conditions and/or consumed nutrition and/or medicaments are analysed in relation to information obtained from medical and biological researches for determining nutrition and/or medication optimal for the user. In addition, the objects of the invention are achieved so that the suitability of the nutrients in the substances to be consumed are determined in relation to the individualised nutrition suitable for the user, at least partly with the help of the nutrition and medication information system utilising learning neurofuzzy systems and methods. The objects of the invention are further achieved so that the mobility of the user and the of system is made possible by arranging at least part of the nutrition and medicament information system of the invention in a mobilised way.

The method for arranging the nutrition and/or medication information service of the invention is characterised in that it comprises the steps of creating a database arrangement, which comprises at least one probability weighting coefficient for at least one gene influencing at least one health property with a certain probability, and at least one probability weighting coefficient for at least one nutrient and/or medical substance influencing at least one health property in a healing or harmful way with a certain probability, delivering information related to the user to the said database arrangement, comparing at least one gene from the user's genetic map with the genetic map information of the database arrangement, and selecting the probability weighting coefficient between the said gene, which is both in the genetic map of the user and in the database arrangement, and at least one health property, which the said gene influences, and further selecting the probability weighting coefficient between the said health property and at least one nutrient and/or medicament, which influences the said health property either in a healing or harmful manner with a certain probability, and forming information describing the suitability of the said nutrient and/or medical substance for the said user with the help of the said probability weighting coefficients.

The arrangement of the invention for arranging the nutrition and/or medication information service is characterised in that the system comprises a database arrangement, which comprises at least one probability weighting coefficient for at least one gene influencing at least one health property with a certain probability, and at least one probability weighting coefficient for at least one nutrition and/or medical substance influencing at least one health property in a healing or harmful manner with a certain probability, comprises means for delivering information related to the user to the said database arrangement, is arranged to compare at least one gene from the user's genetic map with the genetic map information of the database arrangement and to select the probability weighting coefficient between the said gene, which gene is both in the user's genetic map and the database arrangement, and at least one health property, which the said gene influences, and further is arranged to select the probability weighting coefficient between the said health property and at least one nutrition and/or medical substance influencing the said health property either in a healing or harmful manner with a certain probability, and is arranged to form the information describing the suitability of the said nutrient and/or medical substance for the said user with the help of the said probability weighting coefficients.

It is characteristic of the software product of the invention for arranging the nutrition and/or medication information service that the software product comprises a database arrangement, which comprises at least one probability weighting coefficient for at least one gene influencing at least one health property with a certain probability, and at least one probability weighting coefficient for at least one nutrient and/or medical substance influencing at least one health property in a healing or harmful manner with a certain probability, comprises means for delivering the information related to the user to the said database arrangement, is arranged to compare at least one gene from the user's genetic map with the genetic map information of the database arrangement, and to select the probability weighting coefficient between the said gene, which gene is both in the user's genetic map and in the database arrangement, and at least one health property, which the said gene influences, and further is arranged to select the probability weighting coefficient between the said health property and at least one nutrient and/or medical substance, which influences the said health property either in a healing or harmful manner with a certain probability, and is arranged to form the information describing the suitability of the said nutrient and/or medical substance for the said user with the help of the said probability weighting coefficients.

Some advantageous embodiments of the invention are disclosed in the dependent claims.

Compared with the state-of-the-art solutions, considerable advantages are achieved with the help of the present invention. The method of the invention makes possible the mobility of the user and the fast and easy use of the invention irrespective of time and place. The method of the invention also makes possible to utilise the newest medical and biological research information and to use the information disclosing the user's genetic properties, possible illnesses and nutrient limitations caused by these, when determining the individualised nutrition and/or medication suitable for the user and/or when determining the suitability of nutrients in a certain food for the user. For example, the amounts of components contained in the user's daily dose of nutrition and/or medicament and possible adverse effects to the user's health or other effects, for example, to a certain illness, such as hypertension and allergies, can be assessed with the help of the invention. With the invention, it is also possible to determine the medication possibly needed by the user.

The amounts, quality and proportions of nutrients in a daily or possibly a longer-term dose of nutrition and/or medicament and the possible adverse effects can advantageously be assessed taking exactly into account the quality and amount of nutrients and/or medical substances consumed by the user within a certain time. In addition, the invention can be used for observing the proportions of different nutrients and/or medical substances consumed and their effect for achieving the optimal nutrition and metabolic state and as optimal medication as possible to be tailored for the user.

In addition, the user and/or the medical personnel treating the user can observe the user's eating habits, the amounts and proportions of additives, nutrients and other respective substances acquired daily, and also the deficiencies of some substances in real time. With the help of the invention, the medical personnel or some other authorised quarter can also determine nutrition information concerning the user and/or some other general nutrition information to the system in real time, in which case the system can immediately take into account the changes made. Further, the invention also makes it possible for restaurants to at least partly monitor the nutrient amounts acquired by the user. With the help of the invention, restaurant personnel can also be easily instructed in preparing the food portion of the user or a customer using the invention so that the composition of the food portion is optimal in relation to the user's metabolic state, energy consumption, genetic background, illnesses or latent illnesses, allergies and likings.

With the help of the invention, the medical personnel can also fast and easily find out about the user's possible nutrient and/or medical substance limitations, for example, when planning and realising the medication intended for the user. It is still possible with the invention to prepare the food portions to be made for the user to correspond to the individualised dose of nutrition identified for the user, for example, by adding some nutrient components identified by the nutrition information service to the food portions to be eaten by the user.

With the help of the invention, also the producers of substances and quarters responsible for the logistics and merchants can be delivered information, among others, on the effects of the use of certain pesticides and the amount of the pesticides used on foodstuffs treated with the pesticides, and also on the consumption and demand of some nutrients, foodstuffs and/or medical substances. The invention also makes it possible for the producers of foodstuffs to feed to the nutrient system of the invention information at least partly, for example, on the quality, type and quantity of fertilizers used by them, and on other matters relating to the health properties of the foodstuff, such as environmental conditions. Further, the invention makes it possible for the manufacturers of pesticides and preservatives to feed to the nutrient system of the invention information at least partly, for example, on substances in the pesticides and preservatives produced by them, such as components causing cancer, and on their quantities in the pesticide and/or preservative in question. In addition, also the manufacturers of medical substances can supply the system of the invention with information related to medical substances, such as information on effective agents, their amounts and effects.

The invention especially offers the user a possibility to get real-time feedback of the suitability of the food and/or medical substance bought, ordered, consumed or intended to be consumed by the user, taking into account his health and metabolic state, genetic background and structure, genotype, functional state of the genes, illnesses, previously consumed nutrition and/or medicament, and essential scientific research information, because especially in the past years, the medical and genetic researches have more and more often found a connection between a certain illness and a certain gene. Scientific research information can, for example, be gathered from medical articles, and information processed into a form to be understood by the database arrangement of the invention. As raw data, the medical research information can be the following, for example:

genetic variations of beta1 and alpha2C adrenergic receptors can together have an influence on the increased risk to fall ill with heart disease. This two-locus genotype requires specific treatment with alpha2 adrenergic receptor antagonist or beta adrenergic receptor antagonist or both (NEJM, 2002; 347; 1135-1142, is shown), people with the genotype of methylenetetrahydrofolate reductase (MTHFR), which is a genetic change leading to high homocysteine levels, have a 16 percent higher risk to fall ill with cardiovascular disease than people without this genetic change. The risk is especially high, if the genetic change is connected to low folate levels. Thus, increasing the folate level with the help of a diet is advantageous for people with the MTHRF genotype (JAMA, 2002; 288; 2023-2031), it has been presented that the polymorphism of the angiotensin gene and angiotensin convertase gene increases the risk to fall ill with hypertension and cardiovascular disease. In the publication N. Engl. J. Med. 2002; 347; 1916-23, it has been expressed that polymorphism in the connexin 37 gene in men and in the I gene of the type of plasminogene activator inhibitor and in the stromelycin-1 gene in women is connected with the increased risk to get a cardiac infarct (J. Hum. Hypertens 2002; 16(11): 789-93), and it is presented that mutations in the DARD15 gene are connected to the generation of inflammatoric bowel infection (Am. J. Hum. Genet. 2002; 70:845-857).

According to an embodiment of the invention, the user can also be offered a prescription service, in which case the invention can suggest the user a nutrient, a food portion containing a nutrient and/or medication for achieving the nutritive and metabolic state optimal for the user. With the help of the method and system of the invention, the user can especially be suggested optimal medication, taking into account at least one illness of the user and at least one piece of genetic information.

Among others, the following concepts are used in this patent application:

"User" is any individual or group of individuals, which can use the information system of the invention, and the information concerning the state of health and genetic background of which considered sufficient for the system can be delivered to the system, and the nutrition information of the product consumed or ordered or intended to be consumed by which can be delivered to the system for identifying the nutrition optimal for the user. In addition, user is any individual or group of individuals, to which identified optimal nutrition information can be delivered with the help of the nutrition information system of the invention. The user can be a human being or an animal or a larger entity formed of these, for example, a sports team engaging in a certain sport.

"Reference information" is information concerning a reference group, such as information representing relations between health, illnesses and eating habits characteristic of the said group; for example, information that a certain reference group has a 75 percent probability to become exposed to a certain illness. The reference group can, for example, be a tribe, race or nationality, or some population group, sports group, or profession or illness, for example, hypertension. The smallest element in a reference group can be an individual.

"Nutrient and/or medical substance" is a nutrient significant for the relation between medication and/or nutrition and an illness. A nutrient can typically be, for example, a water-soluble or lipo-soluble vitamin, protein, micronutrient, carbohydrate, amino acid, unsaturated or saturated fat, mineral, soluble or insoluble fibre, flavonoid, other phospholipid or phenolic substance or plant estrogen. In this connection, nutrient can also be understood to comprise harmful substances, such as environmental estrogens. Further, in this application, nutrient can also be understood to be especially a medical substance. Nutrient can also be water.

"Nutrition information" is information representing the nutritive contents of a foodstuff and/or medical substance or food product and/or its suitability for a user.

"Foodstuff", food product, product or food is any nutrient or product fit or unfit to be consumed, such as a food portion, drink or medicament, or a combination of these, which can comprise at least one nutrient and/or medical substance. For example, foodstuff can be a fish and, more specifically, a pike. In this application, foodstuff can also comprise hygienic products, such as washing agents and chemicals, for example, shampoos, makeups and suntan creams, to which the user can be exposed, for example, through skin contact. In addition, foodstuff can also be a medicament, such as a blood pressure medicament.

"Intake limit" is an intake limit comprising the upper and lower limit, defined for a certain nutrient and/or medical substance; for example, with salt, the daily intake limit can be 1-5 g. The intake limit is also typically connected with time limit, within which the nutrient and/or medical substance related to the intake limit should be obtained in an amount which is within the area defined by the lower and upper limits of the intake limit.

"Health property" is a psycho-physical state, such as an illness. The health property can also comprise information, for example, about the user's energy consumption and need.

"Scientific research information" is information obtained from scientific researches, such as biological, medical and psychological researches. In this application, scientific research information especially refers to information about genetics, properties determined by genes, functionality of genes, and connections between different foodstuffs and illnesses, obtained in biological and medical researches. In its minimum, scientific research information comprises information about the genetic backgrounds of different illnesses in relation to nutrition and environmental factors and the effective substances in at least one medicament. Most preferably, in the arrangement of the invention, the said scientific research information is in a processed form so that, for example, a certain probability has been formed between different genes and illnesses, to which the said gene exposes, with which the said gene causes the said illness.

BRIEF DESCRIPTION OF THE DRAWINGS

In the next section, advantageous embodiments of the invention are explained in more detail, referring to the enclosed drawings, in which FIG. 5a presents an exemplary user interface of the FPC programme for gathering information about the food products consumed by the user in accordance with the present invention, FIG. 5b presents an exemplary user interface of the FPC programme for gathering information about the user's energy consumption and operational environment in accordance with the present invention.

DETAILED DESCRIPTION OF THE PREFERRED EMBODIMENTS

Figure 1:
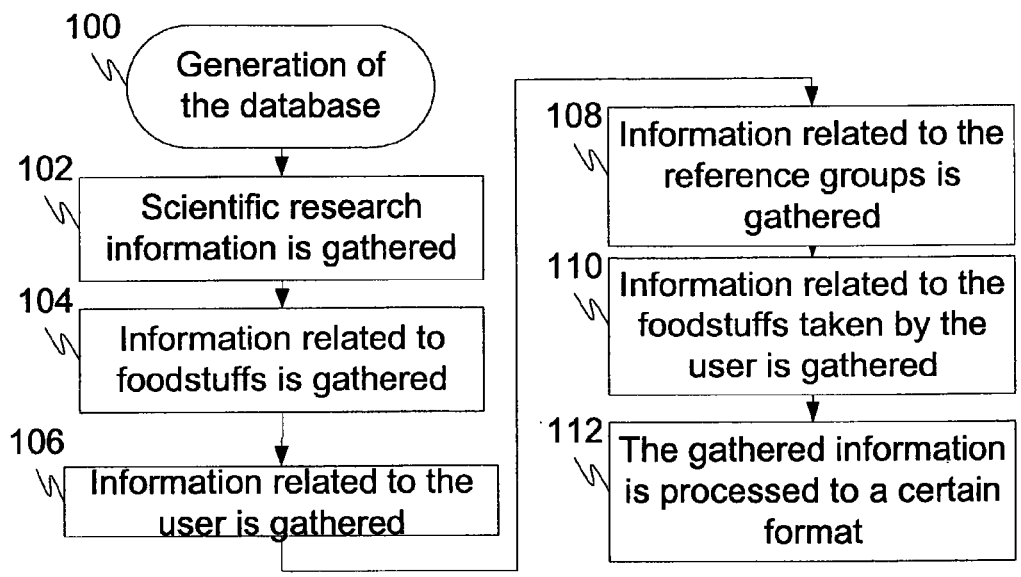
FIG. 1 is a flowchart of an exemplary method for creating a database in accordance with the present invention.

FIG. 1 is a flowchart of an exemplary method 100 for creating a database in accordance with the present invention, in which method information needed by the information service of the invention is gathered from different sources for generating the individualised nutrition and medical information intended for the user. The method of the invention advantageously utilises scientific research information, such as research information obtained from medical and biological researches, which it can gather in step 102. The scientific research information gathered in step 102 can comprise, for example, information about the connections between different illnesses and substances, such as microbes, prions, listeria, salmonella, mould, mercury, lead, nitrates, nitrites, additives, pesticides, antibiotics, salt, coffee, alcohol, cholesterol, mutagens in the drinking water, radiation, sugar, refined food and excessive or too small amount of energy, deficiency of nutrients and protective agents, and oxygen radicals.

Scientific research information can also comprise information, for example, about the effects of water-soluble and lipo-soluble vitamins, proteins, micro-nutrients, carbohydrates, amino acids, saturated and unsaturated fats, minerals, soluble and non-soluble fibres, flavonoids, other phospholipids and phenolic agents, plant estrogens and environmental estrogens on the health properties of a human being or some other living organism. Most preferably, the scientific research information comprises information about the genetic backgrounds of different illnesses in relation to nutrition and environmental factors. In the system of the invention, such information can be reported, for example, in numerical form as probabilities, with what probability an agent causes a certain illness and with what probability a certain nutrient and/or medical substance protects from a certain illness. In addition, the system can contain certain intake limits for substances so that the probability, with which the said substance causes a certain illness, is dependent on the amount of the substance consumed and is especially high, if the amount of the substance consumed within a certain period, for example in a day or a week, exceeds or is below the intake limit for the said substance. The intake limits can be individualised, and they can, for example, be of the format: NaCl (table salt): 1-5 grams a day.

The scientific research information gathered in step 102, such as medical and biological information can, for example, be information about what illnesses and/or symptoms certain substances probably cause either to all human beings or, for example, to some groups of human beings, such as tribes, races or even families or individuals. For example, information gathered in step 102 can comprise information that obesity and western nutrition cause diabetes, cholesterol and salt cause cardiac and vascular disease and osteoporosis, western nutrition causes allergies and asthma, environmental estrogens and western nutrition cause hormone-dependent cancers, carcinogens cause cancer of the colon, fibres protect from the cancer of the colon, and that some infections cause a certain type of rheumatism.

However, it has to be noted that the disclosed example is very broad and that, with the help of the invention, the connections between the consumed nutrition and a nillness in relation to the genotype of an individual or a group of human beings can be assessed in a considerably more sophisticated and exact way, and further, the joint effect of several different nutrients and the environment and at least one gene of an individual can be taken into consideration, in which case it is not necessarily possible to draw direct conclusions, in which, for example, salt would necessarily cause cardiac and vascular disease and infection rheumatism. Information can be fed to the system especially in a processed form and so that the said probabilities are characteristic of a certain individual or group. Part of the probabilities can especially be general truths and part characteristic of an individual.

In addition, the scientific research information to be gathered in step 102 can comprise, for example, information reported and researched by the manufacturers of pesticides and additives or other respective substances about the pesticides and additives manufactured by them; for example, information about what substances the pesticide and additive manufactured by the producer in question contains, and in what amounts. The information gathered in step 102 can also be obtained from literature or any databank understood by one skilled in the art.

In step 104, nutrition information related with foodstuffs is advantageously gathered. For example, nutrition information can be obtained directly from the producers of foods or foodstuffs, quality control organs, and merchants, but also from databanks. The nutrition information to be gathered in step 104 advantageously comprises information about substances in foods and foodstuffs, such as microbes, prions, listeria, salmonella, mould, mercury, lead, other heavy metals and harmful substances, nitrates, nitrites, additives, pesticides, insecticides, environmental poisons, antibiotics, salt, coffee, alcohol, cholesterol, mutagens, radiation, sugar, amount of energy, nutrients, protective agents, oxygen radicals, water-soluble and lipo-soluble vitamins, proteins, micro-nutrients, carbohydrates, amino acids, saturated and unsaturated fats, minerals, soluble and insoluble fibres, flavonoids, other phospholipids and phenolic substances, plant estrogens and environmental estrogens.

Nutrition information can also comprise information about environmental conditions of the food or foodstuff in question, such as in what temperature and moisture the product has been grown, preserved and transported and information about how long the product has been in each state. Nutrition information can also comprise information about the geographical place of cultivation of the said food or foodstuff, its soil bacteria or other soil information, in which case information about substances harmful to the health or other properties possibly contained in the soil and that have possibly come out in the soil researches of the area in question can be combined with information about the foodstuff. Nutrition information can also comprise information about how much and what kinds of pesticides and/or preservatives have been used in the growing and/or manufacture of the said foodstuff. The database of the invention also comprises information related to the user, which is gathered in step 106. Information related to the user can be, for example, information about the user's age, gender, weight, length, genetic background and structure, genotype (DNA), functional state of genes, tribe, group, nationality, illnesses, allergies, mental state, medication, living environment, working environment, type of work, family relations, individual history, and work and sports performance. Information concerning the user can also be a value or information about the fat percentage, blood pressure, blood sugar, hemoglobin and/or cholesterol.

Preferably information related to the user is a sufficient piece of information about the user's genetics, functionality of genes and/or physiological characteristics, on the basis of which the user's nutritive and medical basic needs can be determined. With the help of information related to the user, also the limitations caused by illnesses can be taken into account and found out for the manufacturing process of a food portion to be manufactured to the user, or for the preparation, planning and realisation of medication intended for the user. In addition, information related to the user can comprise information describing the user's likings and dislikings, and information describing the user's hobbies and energy consumption both at work and in free time. In this case, an optimal food portion can be planned for the user with the help of the information service of the invention, for example, a tablet, capsule, pressed piece, powder, grease mixture, oil, ice cube, or food or drink mixture, taking into account the information of the reference group and the user. The reference group can be, for example, sportsmen, such as swimmers, short and long distance runners, shooters or golfers.

According to an embodiment of the invention, a dose of nutrition, which can also contain some medicament or be dose of medicine, can be realised, for example, with a certain dispenser, which can be in telecommunications connection with an information system of the invention. In this case, the information system can supply the dispenser with information about what the dose of nutrition and/or medicament to be delivered to the user should be, what substances the dose should contain, what substances should not be included in the dose, and further, possibly information about how the dose should be manufactured. For example, the dispenser can contain storages and/or containers comprising components to be mixed to the dose, in which case the dose of nutrition and/or medicament optimised for the user can be manufactured automatically on the basis of feedback from the information system of the invention. According to an embodiment of the invention, the dispenser can also comprise at least part of the information unit of the information system of the invention. Information related to the user to be gathered in step 106 can also comprise information about the user's diseases of the locomotoric system, depression, cardiac disease, hypertension, allergy, asthma, headache, migraine, mental illness, illnesses caused by alcohol, dementia and hormone-dependent cancer, or other illness or disorder.

According to the invention, it is also possible to gather information connected with the reference groups in step 108, the information comprising, for example, information about what kind of eating habits certain reference groups have, what kind of nutrients and/or medical substances and/or harmful substances they typically get in the nutrition consumed, in what kind of environmental conditions they live and/or work, what is their genetic background, and what illnesses are common in the said reference group. Such reference groups can be, for example, tribes, races and nationalities, such as PIMA Indians, Japanese, Eskimos, Finns, persons in eastern Finland, East/West Germans, Slavs and Australians. Alternatively, the reference group can also be a reference group representing a certain profession group, such as office employee, fireman, forest worker or diver.

In step 110, according to the invention, information can be gathered that is related with foods and foodstuffs and/or medical substances consumed or intended to be consumed by the user. The information to be gathered in step 110 can preferably comprise information, for example, about the quantity and quality of the substance consumed or intended to be consumed by the user, its age, last selling date or last date of use, nutrition content and information about the substance itself, such as that the food is a fish, more specifically a pike, or a medicament, more specifically penicillin. Further, the information can comprise information also about the salesman and shop who sold the substance, or restaurant or producer, and quality control organs, which have possibly handled the substance. Still, the information gathered in step 110 can comprise information also about the possible processing and/or manufacturing method of the substance, such as a cleaned pike, which has been grilled over a fire.

The information to be gathered in step 110 can also be other information related with the substance, such as information formed by the producer of the substance, or possibly by the quality control organ, which examined the substance; the information can comprise, for example, information about agents in the substance, such as microbes, prions, listeria, salmonella, mould, mercury, lead, other heavy metals and harmful agents, nitrates, nitrites, additives, pesticides, insecticides, environmental poisons, antibiotics, salt, coffee, alcohol, cholesterol, mutagens, radiation, sugar, amount of energy, nutrients, protective agents, oxygen radicals, water-soluble and lipo-soluble vitamins, proteins, micro-nutrients, carbohydrates, amino acids, saturated and unsaturated fats, minerals, soluble and non-soluble fibres, flavonoids, other phospholipids and phenolic agents, plant estrogens and environmental estrogens.

The information gathered in step 110 can also comprise information about the environmental conditions of the said substance, such as food; for example, in what kind of temperature and moisture the product has been grown, preserved and transported, and information about how long the product has been in each state.

Information delivered in steps 102-110 can most preferably be delivered to the information system with the help of the program "FoozPuzzle-Communicator" (FPC program). The FPC program makes it possible to deliver information directly to the information system in an advantageous document format. The user interface of the FPC program can be designed especially according to the needs of a single user, producer and quality control organs of the substances, merchant, restaurant personnel or medical personnel.

According to an embodiment of the invention, the FPC program can be run, for example, on a general server, in which case the FPC program can be used via a data network, such as Internet or digital television, or with the help of a mobile station. The user interface of the FPC program can advantageously be, for example, a form according to the XML and/or XML derivative languages to be offered in the Internet. According to the invention, the information system can be supplied with information also in some other document format, in which case it can be changed to the XML format or the format of XML derivative languages for further processing. According to an embodiment of the invention, at least part of the FPC program can be downloaded to the computer of the user supplying information, to digital television or mobile station, or some other data processing device known by one skilled in the art, such as a PDA device or even a smart card.

Information can be delivered to the system of the invention preferably in a pre-processed form, for example, in electronic form with the help of a form according to XML and/or XML derivative languages, or alternatively, information can be processed to a certain form understood by the system in step 112, for example, manually, or with the help of a system using fuzzy logic. In the processed form, information can be, for example, probabilities, with which a gene exposes to a certain illness. Further the system, in which the information is in processed form, can comprise correlations between different pieces of information so that, for example, the determination of the overall effect of several different genes, nutrient and/or medical substance on a certain illness can be calculated on the basis of the correlations, which can be probabilities.

The invention does in no way restrict the quality of information gathered in steps 102-110, but the information can be of any type, however, preferably information relating to nutrition, medicaments, and to the prevention of illnesses or to the prevention of the worsening of illnesses with the help of these. The information can, for example, be any information come up in scientific researches, any information related to the produced foodstuffs or foods and medical substances, any information related to the user or users or reference groups, or any information related to substances consumed by the user or users, or information describing the connections between substances contained in nutrients or medical substances or medicaments and different illnesses, especially probabilities that a certain nutrient or medicament effects a certain illness either in a healing or harmful manner with a certain probability.

Further, it has to be noted that one skilled in the art can form the database according to the invention also when the order of the steps shown in FIG. 1 is different. In addition, it has to be noted that at least part of the steps 100-112 can be repeated arbitrary times in the method.

Figure 2:
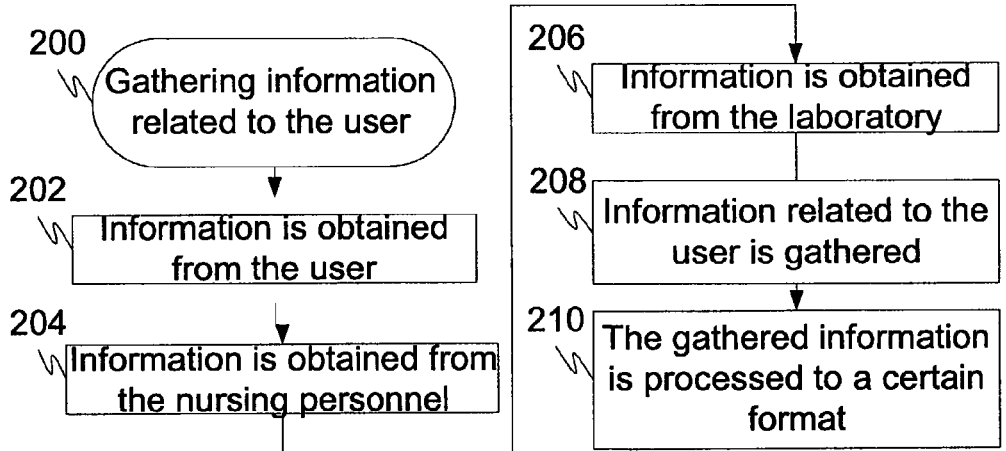
FIG. 2 is a flowchart of an exemplary method for gathering information related to the user in accordance with the present invention.

FIG. 2 is a flowchart of an exemplary method 200 for gathering information related to the user according the present invention. Part of the information related to the user can be gathered from the user himself in step 202. In step 202, the user can deliver information about himself, for example, likings and dislikings concerning foods, and information about illnesses, energy consumption, working environment, hobbies and family relations, to the information system of the invention. The information supplied by the user can be any information reported by the user, which the user can deliver either in numeric format, with the help of a certain code or form, such as a paper form or an electronic form, or alternatively, with the help of free-format text. An electrical form is preferably according to XML and/or XML derivative languages, for example, a form available in the Internet.

The user can deliver his information to the information system, for example, via the Internet, e-mail, digital television or mobile station, by letter or fax or, according to one embodiment, also by phone. Most preferably, the user can deliver the information about the user to be gathered in step 102 to the information system with the help of the FPC program according to the invention.

More information related to the user can be acquired in step 204 with the help of the medical personnel possibly treating the user. The medical personnel treating the user can be given at least partial permission, for example, with the user's consent, to update information describing the user's physiological and psychological state to the information system of the invention. According to an embodiment of the invention, the medical personnel can update information concerning the user's illnesses, possible changes in the illnesses and/or the user's medication to the information system. In addition, in step 204, the medical personnel can also update other information essential for the user's medication, effective agents and amounts of the medicaments, user's behaviour or other special feature to the information system.

In step 206, laboratory results concerning the user, such as results of clinical chemistry, can be updated to the information system. The information to be gathered in step 206 can comprise information, for example, on the user's hemoglobin values, cholesterol values and glucose values from a certain time. The laboratory results concerning the user can be delivered to the information system of the invention, for example, by the laboratory personnel or the medical personnel handling the results or, alternatively, the laboratory results can be delivered to the information system also from the laboratory measuring equipment automatically measuring the values.

Information related to the user's nutrition habits can be gathered in step 208. According to one embodiment of the invention, the information can be obtained at least partly from the systems of shops and restaurants selling foods, foodstuffs and food portions, the systems being able to identify the user and register the composition of the food or food portion bought and/or consumed by the user, and further deliver the nutrition information about the food or food portion to the information system of the invention together with the user's identification data.

Identifying the user can be performed, for example, on the basis of a user ID and password, with the help of information integrated to a magnet card, smart card or barcode, or with the help of any method known by one skilled in the art. The identification can, for example, be performed so that the user's data terminal equipment comprises a unit at least partly in accordance with the invention needed for the formation of individualised nutrition information, information essential for the identification of the user being integrated to the unit. In this case, the systems of shops, restaurants and/or other organs essential for the nutrition information, and those of the medical personnel and pharmacies can identify the user by reading the user's information from the user's data terminal equipment, such as a smart card or mobile station, for example, with the help of a method utilising short-range radio technology, such as Bluetooth, or an infra-red receiver.

Nutrition information on a nutrient and/or medical substance or food portion can be delivered to the information system according to the invention together with the user's identification data, in which case, according to one embodiment, the user can browse the delivered nutrition information of the nutrient and/or medical substance or food portion, using his own data terminal equipment, and either separately accept or reject at least part of the information delivered to the information system. In this case, the information accepted by the user can later be utilised upon determining nutrition and/or medical information optimal for the user, and to destroy information rejected by the user from the system.

Further, the information can be delivered to the system of the invention preferably in pre-processed format, for example, in electronic form with the help of a form according to XML and XML derivative languages or, alternatively, the information can be processed to a form understood by the system, for example, manually or with the help of a system using fuzzy logic in step 210. In the processed form, the information can, for example, be information identifying the substance consumed by the user, such as NaCl, and information describing the amount of the consumed substance, such as 4.2 g. According to an embodiment, for example, information describing a liking can be a weighting coefficient, such as Chinese food 65%, fish food 25%, and grilled food 0%, in which case the system can take into account the user's liking with the help of the weighting coefficient.

It has to be noted that one skilled in the art can gather information related to the user also when the order of the steps shown in FIG. 2 is different. Further, it has to be noted that, in the method, at least part of the steps 200-210 can be repeated arbitrary times. In addition, the information to be delivered in steps 200-208 can be delivered to the information system most preferably with the help of the FPC program according to the invention.

Figure 3:
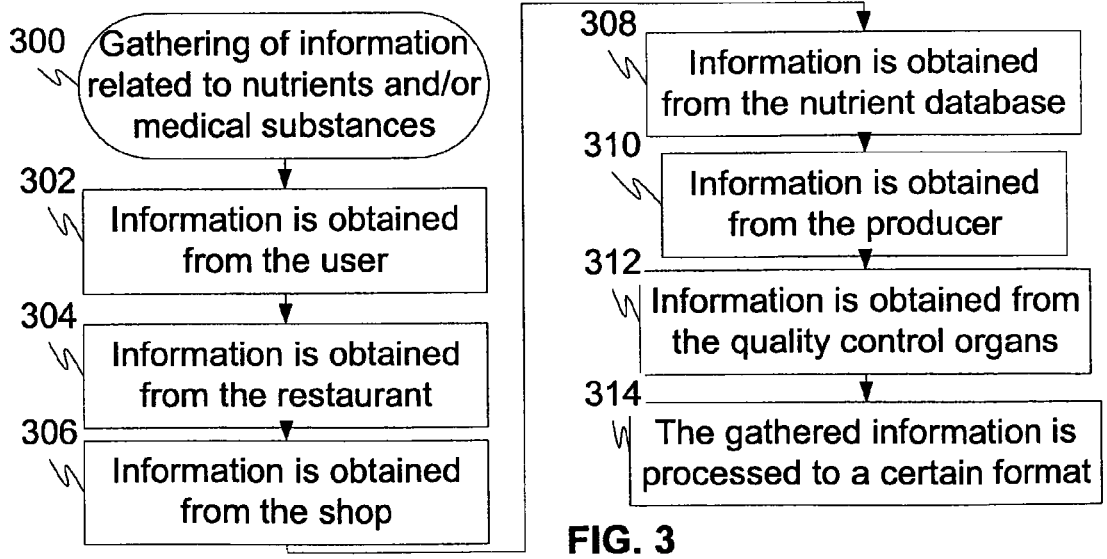
FIG. 3 is a flowchart of an exemplary method for gathering information related to foods consumed by the user in accordance with the present invention.

FIG. 3 is a flowchart of an exemplary method 300 for gathering information related to nutrients and/or medical substances consumed by the user in accordance with the invention, in which method the user himself can deliver information about substances consumed by him to the information system of the invention in step 302. The information delivered by the user can, for example, be exact information about nutrients, amounts and proportions of nutrients contained in a foodstuff, food and/or medicament. Alternatively, information concerning a consumed foodstuff and/or food can, for example, be the following: "300 grams of pike grilled over a fire, slightly spiced with salt". In addition, besides information about a nutrient and/or medical substance delivered by the user, he can also deliver information relating to the time of consuming the substance in question.

The user can deliver the information about the foodstuffs, nutrients and/or medical substances consumed by him in step 302 either in numerical form, with the help of a certain code or form or, alternatively, as free-form text. The user can deliver his information to the information system, for example, via the Internet, e-mail, digital television and mobile station, by letter or fax or, according to one embodiment, also by phone. Most preferably the user can deliver the information to be delivered to the information system in step 302 with the help of the FPC program according to the invention.

Information related to nutrients consumed by the user can also be gathered from the systems of restaurants visited by the user in step 304, when the user so wishes. For example, the user can give his own information service identifier, in which case the restaurant's system can deliver information on the product ordered by the user, such as a food portion or drink, to the information system. The information on the ordered product can comprise, for example, information about the name of the ordered product, such as pepper sauce and pepper steak (300 grams) made of bovine fillet, 100 grams of French fries, and 0.5 liters of III beer, in which case the information system can search more exact nutrition information concerning the product in question from its own database equipment. Alternatively, the restaurant's system can report also more exact nutrition information related to the product, such as energy, 3,400 kJ; protein, 120 g; fat, 47 g; carbohydrates, 80 g; vitamin B1, 10 mg; and fatty acid concentrations and distributions, and amounts and concentrations of amino acids. The system of the restaurant can further deliver information, for example, about the manufacturing method of the food portion prepared by it, or other special information, which the databases of the information system do not possibly have. Such information can, for example, be information related to nutrients added by the restaurant itself.

Information related to foodstuffs, foods, nutrients and/or medical substances bought and consumed by the user can also be gathered from the systems of the shops visited by the user in step 306, when the user so wishes. For example, the user can give his own information service identifier, in which case, for example, the barcode reader system at the cash counter of the shop can deliver information about the product bought by the user to the information system. According to one embodiment, the user can also make an agreement with a shop used by him, in which case, as the user shows, for example, his client card to the cashier, information about the foods and medicaments bought by the user are automatically relayed to the information system of the invention so that, according to one embodiment, the user can still at a later stage approve or reject at least part of the information delivered to the information system, for example, by using his own data terminal equipment. Alternatively, the user can set the system of the invention at least partly in his data terminal equipment to a state in which the organ delivering information to the information system can read, besides the user's identification information, also the status information of the system from the user's data terminal equipment and also deliver the status information to the information system, in which case the information delivered to the information system can be accepted and analysed immediately.

In step 308, more exact information delivered to the information system about foodstuffs, foods, nutrients and/or medical substances bought and/or consumed by the user can be, for example, searched from the database of the information system of the invention. This can be done, for example, when not enough information or not at all information describing the product's nutrition information has been delivered to the information system. In step 310, the information system can be supplied with information related to foodstuffs, foods, nutrients and/or medical substances bought and/or consumed by the user, for example, from the product's producers. This can be done, for example, in a situation in which the information about a product bought or ordered or consumed by the user has been delivered to the information system, but however, the information system does not contain enough information about the nutrient information of the product in question. Likewise, in step 312, information about products bought and/or consumed by the user can be delivered, for example, from different quality control organs.

The information can further be delivered to the system according to the invention preferably in pre-processed format, for example, with the help of a form according to XML and/or XML derivative languages or, alternatively, in step 314, the information can be processed to a form understood by the system, for example, manually or with the help of a system using fuzzy logic. In the processed form the information can be of the form: energy, 3,400 kJ; protein, 120 g; fat, 47 g; carbohydrates, 80 g; and vitamin B1, 10 mg.

Figure 4A:
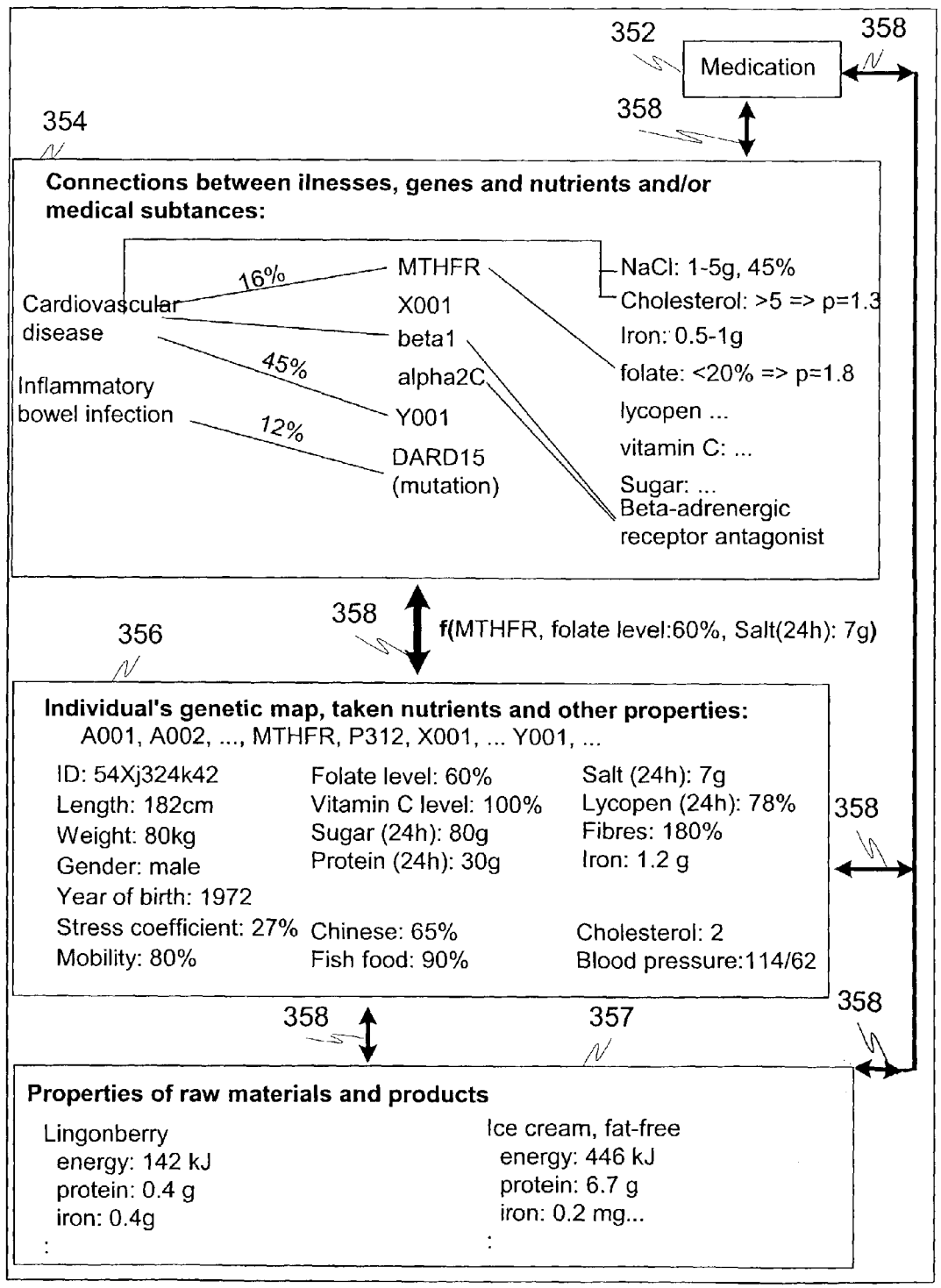
FIG. 4a is a schematic view of an exemplary database arrangement for storing and arranging information in accordance with the present invention.

FIG. 4a is a diagram of an exemplary database arrangement 350 for storing and arranging information essential to the invention. The database arrangement 350 can advantageously comprise several databases and sub-database arrangements 352, 354, 355, 356 and 357. Further, the database arrangement can be a distributed database arrangement, in which case at least one first part of the database arrangement can be stored by at least one first storage medium and at least one second part of the database arrangement can be stored by at least one second storage medium. Information can be transmitted between the database arrangements, for example, by delivering the desired variables as parameters 358, such as at least part of the genetic map of the user, and information about the nutrients and/or medical substances consumed by the user.

Information can be stored to the database arrangement of the invention most preferably in a processed, predefined format. For example, information concerning genes can be fed and stored to the database arrangement on the basis of genetic tests made to an individual preferably in a processed form as facts, with the help of which information about gene forms exposing to illnesses is expressed. Facts concerning genetic tests can be expressed, for example, as character string combinations: "<gene form/-dot>+<result>", in which the result is either positive or negative, or possibly a weighting value, such as a numerical value between −100-+100, describing the weighting value of a gene or its significance in relation to an illness.

Alternatively, facts can be expressed in a form, in which the probability is directly reported, with which the said gene or genotype exposes to a certain illness, such as the fact that persons with the genotype of methylenetetrahydrofolate reductase (MTHFR), which is a genetic change leading to high homocysteine levels, have a 16% higher risk to fall ill with cardiovascular disease than persons, who do not have this genetic ghange. The database arrangement can have a cross reference from the MTHFR genotype, among others, to the folate level, because there exists a scientific fact that the risk to fall ill with a cardiovascular disease is especially high, if the user's folate level is low, in which case the probability to fall ill with a cardiovascular disease can be increased by a certain weighting coefficient, if the user's folate level is below the intake limit for the folate level. For example, if the folate level is below 20%, the weighting coefficient can be 1.8, with which the probability (here 16%) to fall ill with a cardiovascular disease is weighted so that the probability can rise, for example, to 29% (1.8·16%=29%). Taking the weighting into consideration can also be performed by other mathematical methods besides multiplication.

In addition, the said exemplary database arrangement can also have a cross reference to nutrients and/or medical substances, with which deficiency caused by nutrients can be reduced; for example, the said folate level can be raised, in which case the information system according to the invention can suggest the said nutrient and/or medical substance to the user, for example, for raising the folate level and for reducing the risk to fall ill with a cardiovascular disease. Nowadays it is well known that raising the folate level, for example, with the help of a diet is advantageous with persons with the MTHFR genotype.

The facts can alternatively be presented also in some other appropriate way.

Among others, information about analysis results concerning the contents of the researched raw materials/products generated by the quality control unit can also be stored to the database arrangement. The information can be presented, for example, as pairs of substance—measurement result, which are stored to the database as combinations (pairs) of the character string combination and the real number presenting the measuring result needed for the identification of the product; for example, lingonberry, iron 0.4 g. The database can also include a section, in which it is told what is the unit of measure of the real number presenting each measurement result (e.g. mg/100 g). There can be as many said pairs in the database as there are measurements made.

The information generated by the producer can consist of measurement results of the said type and of information concerning growth conditions and growth. The latter category is presented in the database typically as a combination of the character string needed for the identification of the product, the fields determining the location and other conditions of growth (as character strings), and the field specifying calendar information (defining the date: date-month-year, and when required, the time: hours/minutes). Further, also information about transports is stored to the database in an appropriate way. A certain probability or weighting coefficient between the said information and different illnesses, with which the condition defined by the said piece of information or some other parameter exposes to the said illness or protects from the said illness, can be arranged to the database of the invention.

Also information concerning the user's likings and restrictions can be stored to the database arrangement 350. Information describing likings can be stored to the database, for example, as a set of character strings, each of which specifies a single liking, such as "sun-dried tomato a'la Beato" and "onion", or a category of likings, such as "Chinese". Along with every character string, also information about the direction and extent of the liking can be stored, for example, by coding it as an integral number between −100 . . . +100, in which −100 describes total disliking, 0 neutral, and +100 total liking, respectively. Information concerning foodstuff restrictions can be stored to the database, for example, as a set of character strings, each of which specifies the category of a single foodstuff category, such as "gluten", "milk protein" or "E407" (additive, in this example carrageen).

According to one embodiment of the invention, scientific information describing the relations between different illnesses and foodstuffs and/or forms of genes can be fed and stored to the database arrangement 350 by gathering it from scientific publications, for example, in a form of rules, in which the condition part of the rule (can consist of one or several separate conditions) and the inference part are given. A probability value (for example, between −100 . . . +100 or, alternatively, exposure risk increased by 16%) and, according to one embodiment, also the weighting coefficient, such as p=1.8, can be connected to each rule. The said scientific information typically consists of (1) the effect of nutrition on morbidity (positive and negative effects; protective and exposing effects), (2) the effect of medicaments on morbidity (positive and negative effects; protective and exposing effects), (3) the effects of genes on morbidity (positive and negative effects; protective and exposing effects), (4) combinations of all above-mentioned factors (in the rule part, 0–n conditions from each sector). The rules are typically of the format: IF condition 1 AND condition 2 . . . AND condition N SO illness PROBABILITY X, in which X can be a value, for example, between −100 . . . +100. The value −100 can express, for example, that as the conditions are fulfilled, the illness would be avoided with the probability of 100%, and the value +100 can express, for example, that the illness is unavoidable if the said conditions are fulfilled. Alternatively, the values can also be selected from another set of values, and they can be standardised in an arbitrary way according to methods known to one skilled in the art.

The database arrangement of the invention can advantageously be multidimensional, so that upon forming a summary of the overall effect of certain nutrients and/or medical substances, also other levels of the database arrangement 350 can be gone through, such as the level 352, which comprises information about the effects of medical substances on different illnesses together with certain genes. With the help of the database arrangement of the invention, it is possible to chart the joint effect of several factors, for example, in a situation, in which a nutrient exposes to an illness with a certain probability, but simultaneously some other nutrient or a characteristic of some other level, such as the effect of a medicament, influences the said exposure in a protective way.

It especially has to be noted that the database arrangement can have primary probabilities, such as the primary probability of 16% that the MTHFR genotype causes cardiovascular disease or that genes X and Y together cause the illness Z1 with a probability of 20%. In addition, the database arrangement can have secondary probabilities or weighting coefficients; for example, an overdose of NaCl increases the risk to fall ill with cardiovascular disease 1.8-fold, if the person has the MTHFR genotype. The primary probabilities are typically caused by genes and they cannot be changed by a diet, nutrition or medication, when again secondary probabilities or weighting coefficients are due to nutrients and/or medical substances, environmental factors and likings, and they can be changed.

The management and processing of comprehensive information sets in the database arrangement 350 of the invention can be realised, for example, with the help of the Websom method utilising self-organising maps (SOM). The user's information can be at least partly in a processed form, stored to the memory equipment of the system, in which case the said part need not be processed again, unless there have occurred changes in the said information after the previous processing.

Also nutrition and/or medical information can be delivered with the help of the database arrangement of the invention. The nutrition and/or medical information can be produced to an individual in a way, in which the building of nutrient recommendations from completed nutrient alternatives is made possible, on the one hand, and in which restriction conditions, on the other hand, are taken into account, the restriction conditions consisting of basic information, such as nutrient contents, genetic information and personal information, and of the principles in rule form describing the healthfulness of these combinations presenting scientific information.

According to the invention, two different operation models can be presented to the user, such as a model, in which the individual chooses the virtual food plate he wants from the options offered, which options can be presented to the user graphically, for example, with the help of a data terminal equipment of the user. After the user has selected his virtual food plate, the information system of the invention checks the accuracy of the option, for example, in relation to information in the database arrangement 350 and points the deviations and/or directs to better options. Alternatively, a prepared food plate can be formed to be suggested to the user, which plate can be compiled of single foodstuffs, taking into consideration the information and intake limits in the database arrangement 350.

Forming the said food plate to be suggested to the user can be performed, for example, as a series of measures, in which a food plate option is first asked from the individual, and contents information concerning the food plate is gathered from the database arrangement 350. After this, the contents information of the food plate option can be compared with each information category. If there are found inconsistencies, for example, in the intake limits of the substances, or if the user has such a gene, which together with a certain nutrient contained in the food plate option exposes the user to an illness with a probability that exceeds a predetermined limit, such as a probability of 5%, for example, the intensity/significance of the inconsistency can be stored to the read-alter storage. After all contents information has been gone through, the most intensive/important inconsistencies and their effects on the user's health and/or metabolic state can be found out, and a replacing nutrient or contents element can be endeavoured to be found from the database arrangement to replace the nutrient and/or contents element causing the inconsistency.

When as suitable a dose of nutrition and/or medicament as possible has been formed to the user, the dose can be presented to the user, for example, through the user's data terminal equipment with the help of a graphic food plate, the graphic food plate presenting the suitable nutrients and/or medical substances, for example, with the help of a sector, which is proportioned to the amount of the substance. Alternatively, the dose or food plate can be presented also as a text version in plain text, depending on the situation of use.

In the database arrangement 350, the information can be presented, for example, in rule form (so-called Horn clauses supplemented by probability values, cf. R. Kowalski, Predicate logic as a programming language. In Proceedings of IFIP 74, pages 569-574, Amsterdam, 1974. North Holland). The inference mechanism needed to form the suitable dose of nutrition and/or medicament or food plate can be realised, for example, by using the Horn clauses supplemented by probability values. For example, assumption-based inference can be used in the realisation of the inference mechanism (e.g. J. de Kleer. An assumption-based TMS, Journal of Artificial Intelligence. 28. 127-162. 186), likewise the mathematical reasons that are the foundation for this (e.g. A. Dempster. Upper and lower probabilities induced by multivalued mapping. Anneals of Mathematical Statistics. 38. 325-339. 1967. G. Shafer. The Mathematical Theory of Evidence. Princeton University Press. 1976). Alternatively, the inference mechanism can also be realised in some other appropriate way.

It especially has to be noted that the database arrangement can contain considerably more references than in the example of FIG. 4a. For example, one gene can influence several different illnesses, likewise also a nutrient and/or medical substance. In addition, different genes together can generate a different joint effect than all genes taken into account individually.

Figure 4B:
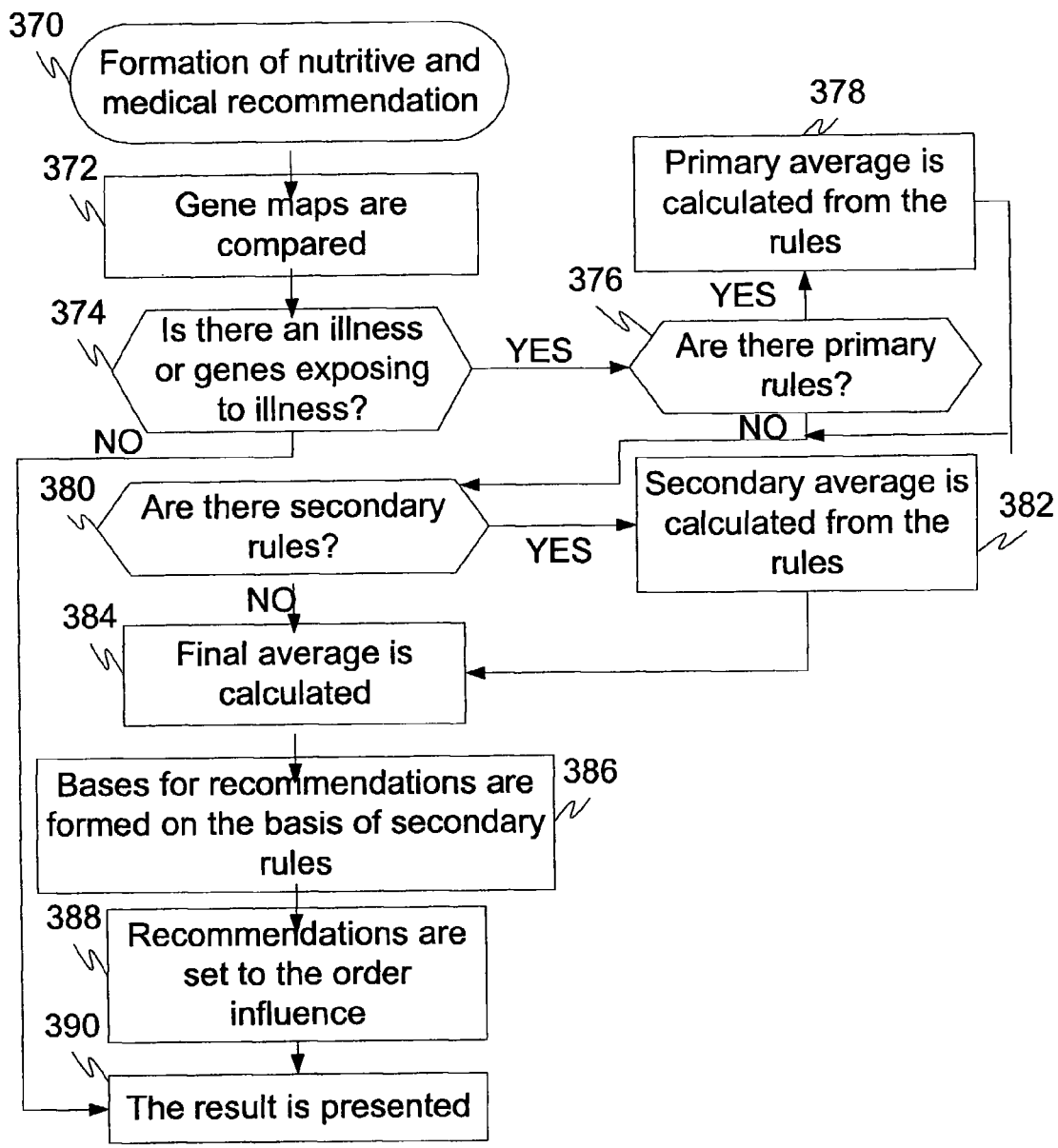
FIG. 4b is a flowchart of an exemplary method for forming individualised medication and/or nutritive recommendation in accordance with an embodiment of the invention.

FIG. 4b is a flowchart of an exemplary method 370 for forming an individualised medication and/or nutritive recommendation in accordance with one embodiment of the invention, in which at least part of the user's genetic map is compared with the genetic map information of the database arrangement of the invention in step 372. In step 372, it is also possible to compare some illness with the illness information of the database arrangement. At least part of the user's genetic map and/or illness information to be compared can be delivered to the database arrangement of the invention to be compared with the help of some data terminal equipment, for example, one mentioned in this application. In step 374 it is examined if a certain illness has been fed to the database arrangement or, alternatively, if the user has a gene exposing to some illness according to the information of the database arrangement of the invention and if yes, the primary rules related to the connection between the gene and illness are examined from the database arrangement in step 376; for example, rules, with which a gene exposes to a certain illness with some probability, and if the user does not have any illness or gene exposing to an illness, one can move to step 390 and present the result or, alternatively, move to step 400 shown in FIG. 4c.

If primary rules were found in step 376, the primary average is calculated from the primary rules and/or probabilities in step 378. For example, if there are the genes X and Y influencing the same illness Z in an exposing way with the probabilities Tx=10% and Ty=20%, the total effect can be calculated from these, for example, by summing and standardising the sum so that the probability does not exceed 100%. The summing operation and standardisation can depend on other connections between the genes, for example, how the gene X influences the operation of the gene Y. According to one embodiment, the probabilities can be summed directly together if the genes, for example, influence the operations of each other so that exposure to an illness is very probable. Alternatively, some other average can be calculated from the probabilities. According to yet another embodiment, a probability can be defined to the joint effect of all genes affecting the illness in some other way, which is not explained in detail in this application, and the result can be fed to the database arrangement of the invention after the said research result has been found. The research result can be, for example, an empirical research result, such as a result that the gene X and Y together expose to the illness Z with the probability of 32%, which is recorded as the primary average in step 378. Further, it has to be noted that the user can have a gene R, which protects from the said illness with a certain probability Tr, in which case the protecting effect can be taken into account in the total assessment by reducing the probability, with which the user is exposed to the said illness.

After the calculation of the primary average or after the step 376 one moves to step 380, and secondary rules related to the said gene and/or illness are examined from the database arrangement, such as rules, by which a nutrient and/or medical substance exposes to an illness or protects from an illness with a certain probability.

If secondary rules were found, the secondary average is calculated from the secondary rules and/or probabilities in step 382. For example, if the nutrient A and medical substance B protect from the said illness Z with the probabilities Ta=15% and Tb=25%, the total effect can be calculated from these, for example, by summing and standardising the sum so that the probability does not exceed 100%. The summing operation and standardisation can depend on other connections between the nutrients and/or medical substances; for example, in what way the nutrient A influences the operation of the medicament B. According to one embodiment, the probabilities can be summed directly together if, for example, the nutrients and/or medical substances influence the operation of each other so that protecting from the illness is very probable. Alternatively, some other average can be calculated from the probabilities. According to yet another embodiment, the probability for the joint effect of all nutrients and/or medical substances influencing the illness can be determined in some other way, which is not explained in detail in this application, and the result can be fed to the database arrangement of the invention after the research result has been found. The research result can be, for example, an empirical research result, such as a result that the nutrient A and medical substance B together protect from the illness Z with the probability of 35%, which is recorded as the secondary average in step 382. Further, it has to be noted that there may be a nutrient and/or medical substance K used by the user, which exposes to the said illness with a certain probability Tk, in which case the exposing effect can be taken into account in the total assessment by reducing the probability, with which the user would have a protection against the said illness.

Further, in steps 380 and 382, information on the nutrients and/or medical substances can be picked from the substances that influence the illness and to create a list of substances, which has as high a protective effect as possible on the said illness.

In step 384, the final average or probability is calculated from the solved primary and/or secondary averages for that the user will fall ill or get a protection against the said illness. The average or probability can be calculated, for example, by summing the probabilities for the exposure to the illness and for the user getting a protection against the said illness, for example, by adding +32% (probability that the user will be exposed to the illness) and −35% (probability that he will get a protection against the illness) together and by standardising the result obtained, for example, so that it does not exceed +100% or be under 0%, in which case the probability for the user to be exposed to the illness would be 0%. Alternatively, it could be reported that the user has a protection with the probability of +3% that he will not be exposed to the illness. The said final probabilities will naturally only be realised if the user consumes nutrients and/or medical substances, the secondary rules of which were used when calculating the secondary average, according to the said intake limits for the said substances.

In step 386, bases for the recommendations can be formed on the basis of the protective nutrients and/or medical substances related to the secondary rules by selecting the nutrients and/or medical substances, the information of which was used in the calculation of the secondary average. In step 388, the said nutrients and/or medical substances can be set to an effective order, for example, so that the substance which protectively influences the illness with the second highest probability, is set second, etc. In connection of the said substances, also the intake limit can be given, which can, for example, be individualised for a certain person or be dependent on some gene or illness and further, for example, on age and situation in life, for example, pregnancy. The final result can be presented to the user in step 390, for example, in a form in which the gene X and Y are reported, exposing to the illness Z with the probability Tz1, and the protective nutrients and/or medical substances A and B, which protect from the illness Z with the probability Tz2, and further the final probability T to be exposed and get a protection, and a list of nutrients and/or medical substances with amounts, the following of which makes it possible to reach the said probability T.

Figure 4C:
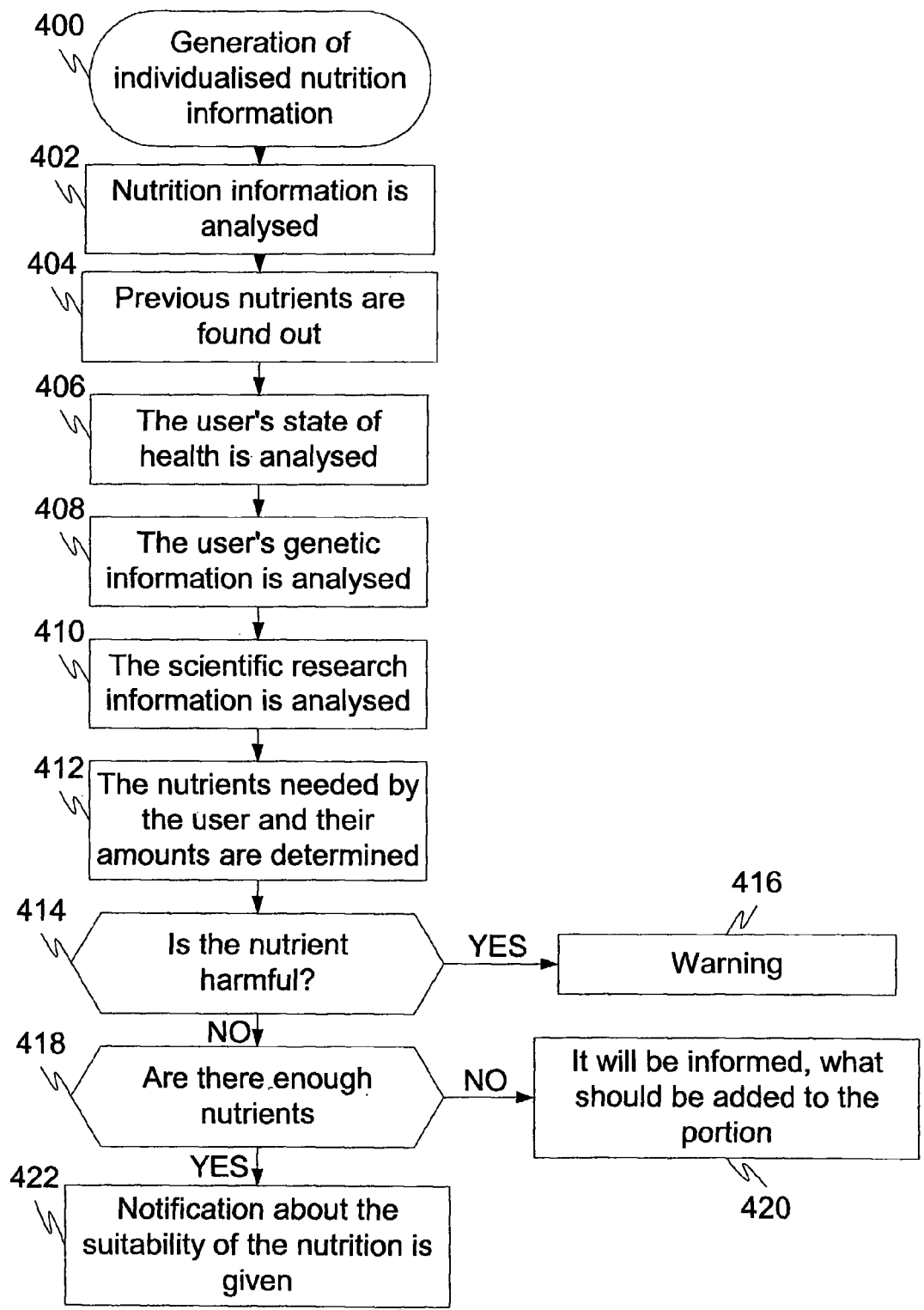
FIG. 4c is a flowchart of an exemplary method for generating individualised nutrition information in accordance with the present invention.

FIG. 4c is a flowchart of an exemplary method 400 for generating individualised nutrition information to the user of the information system according to an embodiment of the invention, in which method the nutrition information on the foodstuff or food intended to be consumed by the user can be received and analysed from the information delivered to the information system in step 402. The delivered information can be, for example, information supplied by the user, a shop or restaurant on the food product consumed, bought and/or ordered by the user. The information can comprise merely the name of the product or other information identifying the product, for example a code, with the help of which the information system can identify the said product, for example, by comparing the code with the information in the databases. The said code can be, for example, a barcode related to the product.

Shop chains, shops and/or restaurants can, for example, have an agreement with the information system of the invention, in which case the shop chains, shops and/or restaurants can deliver information related to their products to the database of the information system so that information on a certain product, such as nutrition information, can be found from the database with the code identifying the product. Alternatively, the information system can find out the information of the product with the code identifying the product from the database equipment of the party that sent the code. The information delivered and to be analysed in step 402 can also be direct nutrition information, for example, the nutrition contents of the product.

Alternatively, also information delivered earlier can be analysed in step 402 for generating the individualised nutrition information and instructions, the instructions guiding the user of the information system of the invention to consume nutrition optimal for the user, for example, for achieving ideal nutritive and/or metabolic state.

The amount and quality of nutrients previously consumed by the user and other information needed in the formation of individualised nutrition information can be analysed in step 404. The information on nutrients previously consumed can comprise information, for example, from one or several days, for example, a week or a month. The information on the nutrients consumed by the user can be found as raw data or, most preferably, in a processed form, for example, in a database, to the information of which the information system of the invention has access.

In step 406, the user's state of health can be observed, analysed and/or assessed, for example, from the database comprising the user's health information, the information system of the invention having access to the information. In addition, in step 408, the user's genotype, i.e. the user's genetic information can be observed; the information can be stored, for example, to a genetic map database, to the information of which the information system of the invention has access. Further, scientific research information can be observed in step 410 at least for the part which is necessary on the basis of the steps 402-408. Scientific research information can be, for example, information of a biological and/or medical research on the connections between an illness and nutrient. Scientific research information can be stored, for example, to a database, to the information of which the information system of the invention has access. The said database can be, for example, an arrangement according to the database arrangement 350 shown in FIG. 4a.

For forming the individualised nutrition information, the physiological and mental state of the user defined on the basis of the measures performed in steps 404-410 and the user's nutritive and metabolic state are assessed in step 412, and this information is proportioned to the analysed nutrition information of the nutrition intended to be consumed by the user in step 402. In step 414, the suitability of the nutrition intended to be consumed by the user, reported in step 402, can be assessed according to the assessment made in step 412. If the nutrition intended to be consumed by the user, reported in step 402, is not suitable or, alternatively, is indeed harmful to the user, warning of this is supplied in step 416.

If the nutrition is suitable, it can be assessed in step 418 if the nutrition intended to be consumed by the user, reported in step 402, has enough necessary nutrients, and if they are found in optimal proportions. If some nutrients should be added to the nutrition intended to be consumed by the user, information about this can be delivered in step 420. The information to be delivered in step 420 can, for example, be an advice to add more vegetables, such as tomato or celery. If the nutrition intended to be consumed by the user is suitable to be consumed, information about this can be delivered in step 422.

The information to be delivered in steps 416, 420 and/or 422 can be delivered, for example, to an address reported by the user, such as the user's mobile station by an SMS message, to the user's e-mail address, via digital television, to the user's service page in the Internet, or by phone. Information can also be delivered by letter or fax. Warning can be delivered also to others, who delivered the information in step 402, for example, to restaurant personnel or medical personnel. Most preferably, the information to be delivered in steps 416, 420 and/or 422 is delivered with the help of the FPC user interface of the invention.

In the method 400, the individualised nutrition information can be formed in a similar way as in the method 380, by calculating the probabilities and/or weighting coefficients representing the suitability of different nutrients. It especially has to be noted that in connection of each piece of information there is at least one probability and/or weighting coefficient and a reference to at least one second piece of information so that at least one probability and/or weighting coefficient can be used when referring to at least one second piece of information and when assessing the final result.

FIG. 5a shows an exemplary user interface 500 of the FPC program for gathering information about food products consumed by the user, and nutrient and/or medical substance information according to the present invention. The user interface 500 shown in FIG. 5a is a typical user interface intended for the user, but also a user interface to be performed in the systems of restaurants, shops and medical personnel can at least partly be similar to the user interface 500.

The user interface 500 can be shown and performed, for example, with the help of a computer, mobile station or PDA device, digital television and/or via the Internet. Alternatively, the user interface 500 can at least partly be presented also on paper. Most preferably, the user interface 500 is a user interface operated via the Internet and/or by mobile phone, in which case the user interface can be realised, for example, with the help of XML or an XML derivative language.

The user interface 500 can comprise the field 502 for defining food products, such as meat, fish and fruits, the field 504 for defining nutrients and/or medical substances, such as energy and proteins, and the field 506 for defining the amount of a food product, nutrient and/or medical substance. The user interface 500 can also comprise the field 508 for defining the manufacturing method of the defined product, and the field 510 for defining the time when the defined product was consumed.

The field 502 for defining the food products can also comprise a sub-menu, in which case the user can define the product in a more exact way. By using the sub-menu, the user can select from the sub-menu, for example, that the fish defined in the field 502 is pike. Likewise, the other fields 504, 506, 508, 510 of the user interface 500 can comprise at least one particularising sub-menu.

Alternatively, at least part of the fields 502-510 of the user interface 500 can be realised in other ways besides sub-menu fields. The fields 502-510 can also be fields, to which text can be written in free form; for example "Pike, 300 g". Also a code defining the desired value for the parameter defined by the field in question can be written to the fields. The code equivalent to the food product pike can be, for example, H1, in which case the user can directly write the code "H1" referring to pike to the food product field 502. The code can typically comprise letters, numbers and/or special characters.

According to one embodiment the user can also have a barcode table describing the different parameters of the fields 502-510 and a barcode reader so that the user can, for example, activate each field 502-510 from the user interface 500 in turn and read the information on the food product, nutrient and/or medical substance, its amount, manufacturing method and time from the barcode table using the barcode reader, such as a barcode pen. According to one embodiment, the barcode can also be alternatively read directly from the product. Certain fields of the user interface can be combined to also relate to several fields in the user interface; for example, the amount field can be combined both to the food product field 502 and the nutrient and/or medical substance field 504. The user interface 500 of the FPC program can also have selection controllers, such as scroll bars 511 and icons/pictures for selecting the parameters.

The user interface 500 can also comprise keys for performing the functions, such as the "Add" key 512, the "Delete" key 514, the "Change" key 516, the "Cancel" key 518, and the "Send" key 520. The "Add" key 512 can be used for adding, for example, several food products to the field 502 or the nutrient field 504. The "Delete" key 514 can be used for deleting parameters already defined from the fields 502-510, and the "Change" key 516 can be used for changing the parameters in the fields 502-510. In addition, the "Send" key 520 can be used for sending the filled-in user interface form 500 to the data server according to the invention. Alternatively, the "Cancel" key 518 can be used for interrupting the operation.

The user interface 500 of the invention can also comprise the field 522 for writing free-form text to the data server. The user interface can further comprise the field 524 for writing the user's user ID and/or password so that one can make sure that outsiders cannot change and/or read the information of other users.

Alternatively, the user interface 500 can also at least partly be presented graphically, for example, with the help of a graphic food plate, in which case the user can add nutrients and/or medical substances and food products intended to be consumed to the food plate using a controller, such as a mouse, keyboard or touch screen, for example, by pressing, pointing or hauling icons and/or pictures presenting nutrients and/or medical substances and food products.

According to one embodiment of the invention, the user interface 500 of the FPC program is a learning user interface so that an own profile can advantageously be made for each user to the user interface. In this case, the user interface can learn the food and drink habits and nutritive and medical habits of each user, for example, according to the times of day so that the user interface is able to anticipate situations and suggest to the user certain food products often consumed by him, nutrients and/or medical substances, amounts, manufacturing methods and/or times. For example, to a user, who eats 250 g of porridge, an egg, two pieces of bread and 2 dl of orange juice each morning and yoghurt, muesli and a banana in the evening, the user interface can suggest the said food products as default value. Then, the user only has to accept the suggestion.

However, it has to be noted that the user interface 500 of the invention for gathering the user's food product information and nutrient and/or medical substance information can also comprise considerably more fields for more detailed identification of the information and considerably more keys or selection controllers for performing different functions. Alternatively, the user interface 500 of the invention can also be realised by using a smaller number of fields, keys and selection controllers than in the embodiment of the user interface shown in FIG. 5a. Further, it has to be noted that, in addition to the said fields, the user interface 500 can include a field, to which the optimal nutrition information and instructions for reaching the optimal nutritive and/or metabolic state generated by the information service of the invention is returned as default value.

Further, it has to be noted that, according to one embodiment of the invention, also the optimal nutrient response formed by the information system to the food portion or graphic food plate reported by the user and intended to be consumed can be delivered to the user with the help of a user interface similar to the user interface 500 shown in the Figure. The response can be at least partly delivered graphically, for example, with the help of an optimal graphic virtual food plate.

FIG. 5b shows an exemplary user interface of the FPC program 550 for gathering information about the user's energy consumption and environmental conditions according to the present invention. The user interface 550 can be presented and performed, for example, with the help of a computer, mobile station or PDA device, digital television and/or via the Internet. Alternatively, the user interface 550 can be at least partly presented on paper. Most preferably, the user interface 550 is a user interface to be operated via the Internet and/or with the help of a mobile station so that the user interface can be realised, for example, with the help of XML or an XML derivative language.

The user interface 550 typically comprises the field 552 for defining the physical performance performed by the user, such as walking, jogging, gym and swimming, the field 554 for defining the duration of the physical performance performed, for example 1 hour and 30 minutes, and the field 556 for defining the amount of the physical performance performed, for example, 7,200 meters. The user interface 550 can also comprise the field 558 for defining the level of difficulty of the physical performance, for example, demanding, average or easy, and the field 560 for defining the time of the physical performance.

The field 552 for defining physical performance can also comprise a sub-menu, in which case the user can define the type of the performance in a more exact way. By using the sub-menu, the user can select from the sub-menu, for example, that the running defined in the field 552 is terrain running. Likewise, also the other fields 554, 556, 558, 560 can comprise at least one specifying sub-menu.

Alternatively, at least part of the fields 552-560 of the user interface 550 can be realised in some other way besides menu fields. The fields 552-560 can also be fields, to which text can be written in free form; for example, "Terrain running, 7,200 m". Also a code defining the desired value for the parameter defined by the said field can be written to the fields. The code equivalent to terrain running can be, for example, Jm, in which case the user can directly write the code "Jm" representing terrain running to the performance field 552. The code can typically comprise letters, numbers and/or special characters.

According to one embodiment, the user can have a barcode table describing the different parameters of the fields 552-560 and a barcode reader, in which case the user can, for example, activate each field 552-560 in turn from the user interface and read the information about the performance, duration, amount, level of difficulty, and time from the barcode table using the barcode reader, such as a barcode pen. The user interface 550 of the FPC program can also have selection controllers, for example, scroll bars 561, for selecting the parameters.

In addition, the user interface 550 can comprise keys for performing the commands; for example, the "Add" key 562, the "Delete" key 564, the "Change" key 566, the "Cancel" key 568, and the "Send" key 570. The "Add" key 562 can be used for adding, for example, several performances to the field 552. The "Delete" key 564 can be used for deleting parameters already defined from the fields 552-560, and the "Change" key 566 can be used for changing the parameters in the fields 552-560. Further, the "Send" key 570 can be used for sending the filled-in user interface form 550 to the data server according to the invention. Alternatively, the "Cancel" key 568 can be used for interrupting the operation.

The user interface 550 according to the invention can further comprise the field 572 for writing free-form text to the data server. The user interface can also include the field 574 for writing the user's user ID and/or password so that one can make sure that outsiders cannot change and/or read the information of other users.

According to one embodiment of the invention, the user interface 550 of the FPC program is a learning user interface, in which case an own profile can be advantageously made for each user to the user interface. In this case, the user interface can learn the physical sports habits of each user, for example, according to the times of day so that the user interface is able to anticipate situations and suggest to the user certain physical performances often performed by the user, their durations, amounts, levels of difficulty and/or times of performance. For example, the user interface can suggest to the user, who walks 1.6 km each weekday morning, and swims 1000 m every Tuesday and Thursday evening, the said performances as default value. In this case, the user only has to accept the suggestion.

Alternatively, the user interface 550 can be at least partly presented graphically so that the user can add information describing his performances by using a mouse, keyboard or touch screen; for example, by pressing, pointing or hauling icons and/or pictures describing the performances, their levels of difficulty and duration.

However, it has to be noted that the user interface 550 according to the invention for gathering information describing the user's energy consumption and environmental conditions can also comprise a considerably higher number of different fields for the more exact identification of the information about energy consumption or environmental conditions and a considerably higher number of different keys or selection controllers for performing different functions. Alternatively, the user interface 550 of the invention can be realised by using a smaller number of fields, keys and selection controllers than in the embodiment of the user interface shown in FIG. 5b. It still has to be noted that, in addition to the said fields, the user interface 550 can have a field, to which the optimal nutrition information and instructions for reaching the optimal nutritive and/or metabolic state generated by the information service of the invention are returned as default value.

Further, it has to be noted that, according to one embodiment of the invention, the information system can also form suggestions for physical performances and to present the optimal physical performance formed by it and the level of difficulty and duration of the performance with the help of a user interface similar to the user interface shown in FIG. 550. The suggestion can also be delivered graphically, at least in part.

Figure 6:
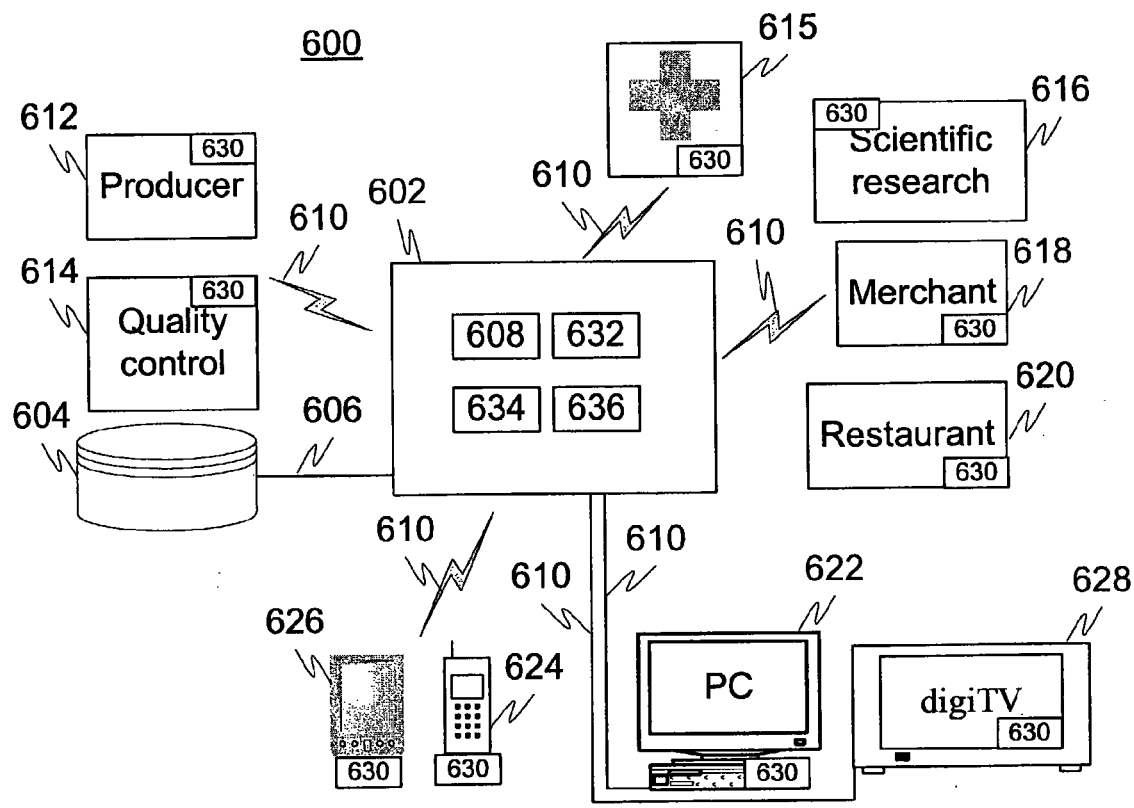
FIG. 6 is a block diagram of an exemplary system for generating individualised nutrition information in accordance with the present invention.

FIG. 6 is a flowchart of an exemplary system 600 for forming individualised nutrition information in accordance with the present invention. The system 600 typically comprises the information unit 602 for gathering different types of information needed in the formation of individualised nutrition and medical information and for forming the individualised nutrition and medical information. Most preferably, the information unit 602 can be, for example, the server 602 in the Internet, comprising equipment needed in the formation of individualised nutrition and medical information, the information connection to which server can also be made via a mobile station. The information unit 602 can produce information alternatively also to the transmission network of digital television.

The information unit 602 typically comprises the database equipment 604 for storing the information. The database equipment 604 can comprise, for example, a database arrangement similar to the database arrangement 300 shown in FIG. 4a. The information can be, for example, information concerning foodstuffs, genetics, biological, medical, analysed biological and medical research, empirical information, and information describing the user and the user's situation-specified information, and information describing the user's environment. In addition, the database equipment 604 can contain information referring to reference groups, such as information related to certain tribes or nationalities, and information related to their possible illnesses, living environment and foodstuffs typically consumed by them. The database equipment 604 can be integrated to the information unit 602 of the information system 600 at least in part or, alternatively, the database equipment 604 can be spread separately from the information unit 602 so that the information unit 602 has the data transmission connection 606 to the database equipment 604.

The information unit 602 typically comprises also the equipment 608 for generating the data transmission connection 606 and 610 with the other parties, such as the producer 612, the quality control unit 614, the medical personnel unit 615, the scientific research unit 616, the shop system 618, and the restaurant system 620. In addition, the information unit 602 can be arranged to be in data transmission connection 610 with the user via a data terminal equipment, such as the computer 622, the mobile station 624, the PDA device 626 and/or the digital television 628.

The information unit 602 can also comprise the equipment 636 for identifying each party, such as the producer 612, the quality control unit 614, the medical personnel unit 615, the scientific research unit 616, the shop system 618, and the restaurant system 620 so that each party 612-620 can deliver information they have formed about different food products and their nutrition contents, or substances contained in the food products, and about possible illnesses caused by certain foodstuffs and their interrelations.

Information about a food product bought or ordered by the user can be delivered, for example, from the shop system 618 and/or the restaurant system 620 to the information unit 602 of the information system 600 automatically in connection of the purchase or order. The identification information of the user, needed by the information system, can be stored, for example, to a magnetic card, in which case the user's magnetic card can be read in connection of the purchase or order, and in which case the information of the food products in the purchase or order are relayed to the information unit 602 of the information arrangement. Alternatively, the user's individualised user ID can be fed into the system of the shop or restaurant, in which case the information of the bought or ordered food product are relayed to the information unit 602 of the information system 600.

The parties 612-628 in data transmission connection 610 to the information unit 602 can advantageously comprise the equipment 630 for performing the FPC program according to the information, for sending and updating the information of the FPC program and for receiving the information to a data terminal equipment 612-628 from the information unit 602. According to one embodiment of the invention, the equipment 630 can also comprise at least partly the information unit 602 of the information system 600 according to the invention for forming individualised and/or optimal nutrition information. The information unit 602 or at least part of the information unit 602 can be downloaded to the data terminal equipment 612-628 of the parties, for example, by a program from some information network, or it can be delivered using means intended for data transmission known by one skilled in the art, for example, on CD ROM or DVD disc.

In addition, the information unit 602 typically comprises the memory equipment 632 and the equipment 634 for processing and analysing the information and for forming individualised optimal nutrition information. The information unit 602 advantageously uses fuzzy logic for analysing information in the database equipment and for forming individualised nutrition information with the help of the analysed information. The nutrition unit can handle and process information using the equipment 602, 608, 632 and 634, for example, with the help of the Websom method utilising the self-organising map (SOM) or, alternatively, information can be processed also manually. In addition, the nutrition unit can also define the reference profile of different parties or elements, such as the user's reference profile, with the help of the equipment 602, 608, 632 and 634.

The information unit 602 can further comprise the equipment 634 for identifying the user, for example, with the help of the user ID and password. The user can also be identified with the identifier of the user's mobile station, such as mobile phone number.

In addition, the information unit 602 typically comprises the equipment 638 for delivering the formed individualised nutrition information to at least one of the following: the producer 612, the quality control unit 614, the medical personnel unit 615, the scientific research unit 616, the shop system 618, the restaurant system 620, or some system of the user, such as the computer 622, the mobile station 624, the PDA device 626, and the digital television 628. The individualised optimal information can also be delivered by letter or fax and, additionally, by dictating on the phone.

It has to be noted that the information to be stored to the database equipment and the data terminal equipment 612-628 of the parties, especially to the mobile stations 624 and 626, can be derived information, which as such does not reveal possibly delicate information about the individual, even when uncovered, but it expressly supports the process concerning the selection of nutrition and medication. For example, the user's mobile station can have information about the user's genetic map, such as part of the genetic map, and information related to the user, such as identifier information (ID).

The data transmission connection 610 used in the system of the invention can be any data transmission connection known to one skilled in the art. Especially, the system 600 can be compatible with at least one of the following data transmission specifications: TCP/IP, CDMA, GSM, HSCSD, GPRS, WCDMA, EDGE, Bluetooth, UMTS, Teldesic, Iridium, Inmarsat, WLAN, DIGI-TV, ISDN, xDSL, RPC, HomePna, and imode. In addition, the information unit 602 and the data terminal equipment 612-628 of the parties can comprise at least one of the following operating systems for performing the FPC program of the invention: Unix, MS-windows, EPOC, NT, MSCE, Linux, PalmOS, and GEOS.

Figure 7:
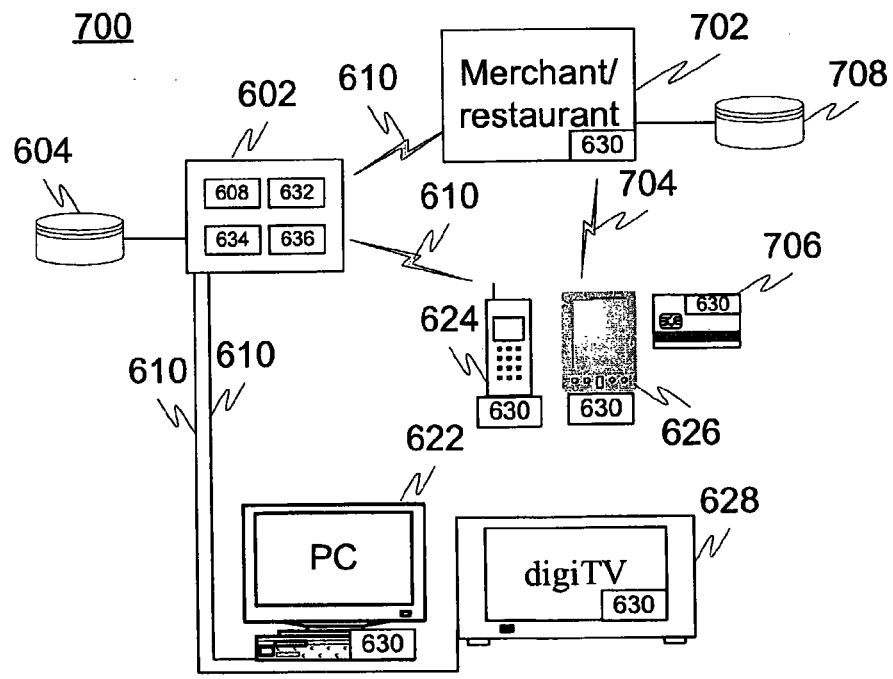
FIG. 7 is a block diagram of an exemplary system for updating the user's nutrition information and for generating individualised nutrition information in accordance with the present invention.

FIG. 7 is a flowchart of an exemplary system 700 for updating the nutrition and/or medical substance information of the user and for generating individualised nutrition information according to the present invention. In the example, the user of the information service of the invention does business with one party 702, such as in a restaurant, shop, gym or similar and/or at the doctor's. The party 702 can comprise the equipment 630 for performing the FPC program of the invention, in which case the system of the party 702 can identify the user of the information service of the invention with the help of his data terminal equipment. The data terminal equipment of the user can be, for example, the mobile station 624, the PDA device 625, or the smart card or magnetic card 706, the data terminal equipment 624, 626, 706 comprising the equipment 630 for performing the FPC program of the invention and/or for making the identification of the user possible.

According to one embodiment, the user can, for example, visit the shop and/or restaurant 702, in which case, for example, when paying for the purchase, the equipment 630 of the system 702 of the shop and/or restaurant identify the user with the help of the equipment 630 in the data terminal equipment 624, 626, 706. The information of the user essential for the information service of the invention can preferably be integrated to the equipment 630 of the data terminal equipment 624, 626, 706. In this case, the system 702 of the shop and/or restaurant can read the user's information, for example, via an infrared or radio link, such as a system utilising the Bluetooth technology 704 from the user's data terminal equipment 624, 626, 706. After having read the user's information, the system 702 of the shop and/or restaurant can send the information about the purchases made by the user to the information unit 602 of the information system of the invention. In addition, the system 702 of the shop and/or restaurant can also comprise the database equipment 708 for storing the nutrition information of the products.

According to one embodiment, the system 700 can have been arranged so that the information about the user's purchases are delivered to the user, in which case the user can confirm the purchases he has made. For example, the user can delete part of the products, or add some additional information to the information, or accept the delivered information. The information is preferably delivered to the user's data terminal equipment, such as mobile station, PDA device, digital television, or computer, for example, as an SMS message or e-mail. Alternatively, the information can be delivered also the user's service page in the Internet.

The party 702 shown in FIG. 7 can also be a unit of medical personnel, in which case, for example, information about the user's health can be delivered to the information unit 602 of the invention in the way described above. The system 700 of the invention can be arranged so that the system 700 uses only the information confirmed by the user when generating nutrition and/or medical information optimal for the user. Alternatively, the system 700 can be arranged so that information about the user's health and/or information about purchases made in a shop and/or restaurant are automatically registered to the information unit 602 so that they can be immediately used for forming the optimal nutrition information directed to the user.

Only some embodiments of the solution according to the invention have been disclosed above. The principle of the invention can naturally be varied within the scope of the patent claims, for example, for the part of details and areas of use of the realisation. The system can especially be applied for forming individualised nutrition information but, however, the invention is not restricted to this, but the invention can also be applied for forming nutrition information of other animals, such as domestic animals and cattle.

In addition, the invention is not restricted to the user of the information unit of one information system only, but the data transmission networks can have several single information systems, which can be connected to each other with the help of data transmission systems known to one skilled in the art.

Further, it has to be noted that the information system of the invention can at least partly be integrated to the user's data terminal equipment.

It still has to be noted that, besides optimal nutrition, also optimal medication can be planned for the user with the help of the invention. According to one embodiment of the invention, with the invention it is possible to prepare a dose of nutrition and/or medicament optimal for the user, for example, according to components so that the effect of nutrients and/or other medical substances on the concentrations, absorption and effect of a medical substance and/or nutrient and/or also of some other medical substances and/or nutrients and on the user's metabolism are taken into account.

In addition, the information arrangement of the invention can give feedback and at least part of the user's information, such as information about allergies, illnesses and likings, for example, to the user's data terminal equipment in the language selected by the user. It still has to be noted that at least part of the system and database arrangements of the invention can be realised with the help of computer software or a software product.

The invention claimed is:

1. A method for offering proposals and/or information about suitability of nutrients, and/or medical substances for a user by communicating via a user's data terminal, the method comprising:

1) establishing data transmission connections between a central server and a data communication network and the user's data terminal, where said data communication network comprises information about relations between genes and health properties, how the genes influence said health properties, information about relations between nutrients and/or medical substances' health properties and how the nutrients and/or medical substances influence said health properties, and a) gathering via said data transmission connection from said data communication network continuously information of an influence of at least one gene and/or at least one gene being in a functional state to at least one health property in a healing or harmful manner with a certain probability, providing cross references between said genes and related health property and providing a numerical probability weighting coefficient of the influence of at least one gene and/or at least one gene being in a functional state to at least one health property in a healing or harmful manner with a certain probability, b) gathering via said data transmission connection from said data communication network continuously information of influences of nutrients and/or medical substances to at least one health property in a healing or harmful manner with a certain probability, providing cross references between said nutrients and/or medical substances and related health properties and providing numerical probability weighting coefficients to nutrients and/or medical substances influencing said health property in the healing or harmful manner with the certain probability, c) gathering via said data transmission connection information of the user's gene and/or the user's gene being in the functional state, and providing a numerical indication in a predefined format of the user's gene and/or user's gene being in the functional state to identify said gene, d) gathering via said data transmission connection from said user's data terminal information, or information pertaining to amounts, about nutrients and/or medical substances consumed and/or to be consumed by the user via an interactive graphical plate displayed by the user's data terminal; followed by 2) comparing by a processing and analyzing equipment of the server indicated user's gene with gene information gathered in step 1a) to find out correspondence;
3) finding by the processing and analyzing equipment of the server health properties related to said correspondence gene via the cross references provided in step 1a);
4) selecting by the processing and analyzing equipment of the server the numerical probability weighting coefficient between said gene and at least one health property, to which said gene influences when being in the normal and/or in the functional state;
5) finding by a processing and analyzing equipment of the server nutrients and/or medical substances related to said health property via the cross references provided in step 1b);
6) selecting by the processing and analyzing equipment of the server the numerical probability weighting coefficients between said health property of step 4) and nutrients and/or medical substances of step 5) influencing the said health property in the healing or harmful manner with the certain probability;
7) comparing by a processing and analyzing equipment of the server information about nutrients and/or medical substances consumed and/or to be consumed by the user gathered in step 1d) and taking into account amounts of the corresponding nutrients and/or medical substances by adding or subtracting their amounts from the recommended amounts;
8) forming individualized optimal nutrition and/or medical substance information with amounts to be consumed by ordering by the processing and analyzing equipment of the server the numerical probability weighting coefficients determined in step 6) to describe the suitability of nutrients and/or medical substances for the user so that the nutrient and/or medical substance influencing to said health property in the most healing manner is offered as the proposal;
9) modifying the amounts of the individualized optimal nutrition and/or medical substance provided in step 8) by adding or subtracting the already consumed amounts of corresponding nutrients and/or medical substances find out in step 7); and
10) communicating via said the information about the nutrition and/or medical substance in the order provided in step 8) and with modified amounts provided in step 9) as a proposal to the user via the user's data terminal at least partly as an interactive graphical plate displayed by the user's data terminal information.

2. The method according to claim 1, wherein the server is communicated via said data transmission connection by at least one numerical probability weighting coefficient for at least one pair to be selected from the following group: at least one gene together with at least one nutrient and/or medical substance influences at least one health property in the healing or harmful manner with the certain probability, and the user is allergic to at least one nutrient and/or medical substance with a certain probability.

3. The method according to claim 1, wherein the nutrients and/or medical substances, which influence said health property in the healing or harmful manner with some probability and the probabilities related to the nutrients and/or medical substances were used when defining the information describing the suitability of said nutrient and/or medical substance to the user, are arranged by said processing and analyzing equipment of the server to such an order that the nutrient and/or medical substance, which has the highest probability to have a healing effect on said health property, is placed as the most important.

4. The method according to claim 1, wherein information related to at least one nutrient and/or medical substance consumed or intended to be consumed by the user is delivered with help of data terminal equipment to said data transmission connection of said server.

5. The method according to claim 1, wherein addition to user's genetic information also user's identifier information (ID), at least part of the user's genetic map, the user's weight, the user's length, the user's sex and/or the user's age is communicated to said data transmission connection of said server, and nutrient information and/or medical substance information consumed by the user, the data terminal equipment is used for delivering amounts of the nutrients and/or medical substances, and that the nutrition information and/or medical substance information of the nutrients and the amounts consumed by the user are registered to said database arrangement cumulatively by the server and so that they can be combined with the user's identifier information.

6. The method according to claim 1, wherein individualized intake limits are set to at least one nutrient and/or medical substance and a notification is formed by said processing and analyzing equipment of the server, if the cumulative amount of said nutrient and/or medical substance during a predetermined time period is higher or lower than said individualized intake limit defined for the user.

7. The method according to claim 1, wherein cumulative amounts of substances of nutrients and/or medical substances consumed by the user within a selected period of time are compared with intake limits set for said nutrients and/or medical substances by said processing and analyzing equipment of the server, at least one nutrient or medical substance is selected, a cumulative amount of which in said period of time is not within the area of the predetermined intake limit, and if the value of the probability weighting coefficient for said substance influencing a certain health property in the healing manner, is above the predetermined limit, a proposal of said nutrient and/or medical substance to be taken by said user is delivered to the user's data terminal via said data transmission connection of said server.

8. The method according to claim 1, wherein information is delivered to the data transmission connection of said server with at least one of the following systems: with the help of a mobile station, PDA device, smart card, magnet card, via the Internet, or via digital television.

9. A system for offering proposals and/or information about suitability of nutrients, and/or medical substances for a user, comprising
    a user's data terminal;
    a central server; and
    a data communication network;
    1) the system being configured so that data transmission connections are established between said central server and said data communication network and said user's data terminal, where said data communication network comprises information about relations between genes and health properties, how the genes influence said health properties, information about relations between nutrients and/or medical substances health properties and how the nutrients and/or medical substances influence said health properties, and
    a) the system being configured to gather via said data transmission connection information of an influence of at least one gene and/or at least one gene being in a functional state to at least one health property in a healing or harmful manner with a certain probability, providing cross references between said genes and related health property and providing a numerical probability weighting coefficient of the influence of at least one gene and/or at least one gene being in a functional state to at least one health property in a healing or harmful manner with a certain probability, b) the system being configured to gather via said data transmission connection information of influences of nutrients and/or medical substances to at least one health property in a healing or harmful manner with a certain probability, providing cross references between said nutrients and/or medical substances and related health properties and providing numerical probability weighting coefficients to nutrients and/or medical substances influencing said health property in the healing or harmful manner with the certain probability, c) the system being configured to gather via said data transmission connection information of the user's gene and/or the user's gene being in the functional state, and providing a numerical indication in a predefined format of the user's gene and/or user's gene being in the functional state to identify said gene, and d) the system being configured to provide by said user's data terminal information, such as amounts, about nutrients and/or medical substances consumed and/or to be consumed by the user via said data transmission connection as a query, where said information is gathered for example by the user's data terminal via an interactive graphical plate displayed by the user's data terminal; the server being configured to perform following functions:

2) to compare by a processing and analyzing equipment of the server indicated user's gene with gene information gathered in step 1a) to find out correspondence;

3) to find by the processing and analyzing equipment of the server health properties related to said correspondence gene via the cross references provided in item 1a);

4) to select by the processing and analyzing equipment of the server the numerical probability weighting coefficient between said gene and at least one health property, to which said gene influences when being in the normal and/or in the functional state;

5) to find by the processing and analyzing equipment of the server nutrients and/or medical substances related to said health property via the cross references provided in item 1b);

6) to select by the processing and analyzing equipment of the server the numerical probability weighting coefficients between said health property of item 4) and nutrients and/or medical substances of item 5) influencing the said health property in the healing or harmful manner with the certain probability;

7) to compare by the processing and analyzing equipment of the server information about nutrients and/or medical substances consumed and/or to be consumed by the user gathered in item 1d) and taking into account amounts of the corresponding nutrients and/or medical substances by adding or subtracting their amounts from the recommended amounts;

8) to form individualised optimal nutrition and/or medical substance information with amounts to be consumed by ordering by the processing and analyzing equipment of the server the numerical probability weighting coefficients determined in item 6) to describe the suitability of nutrients and/or medical substances for the user so that the nutrient and/or medical substance influencing to said health property in the most healing manner is offered as the proposal;

9) to modify the amounts of the individualised optimal nutrition and/or medical substance provided in item 8) by adding or subtracting the already consumed amounts of corresponding nutrients and/or medical substances find out in item 7; and 10) to communicate via said data transmission connection the information about the nutrition and/or medical substance in the order provided in item 8) and with modified amounts provided in item 9) via the user's data terminal, whereupon the data terminal is adapted to receive said communicated information as a response to said query and use it's display means for displaying at least part of said received communicated information as a proposal to the user via an interactive graphical plate displayed by the user's data terminal.

10. The system according to claim 9, wherein the system further comprises at least one data terminal equipment, with which information related to at least one nutrient and/or medical substance taken or intended to be taken by the user is delivered to the data transmission connection of said server as well as also user identifier information, and the server is further arranged to register to the database arrangement the amounts of the nutrients and/or medical substances taken by the user cumulatively and so that they can be combined with the user's identifier information by said processing and analyzing equipment of the server.

11. The system according to claim 9, wherein the database arrangement comprises individualized intake limits for at least one nutrient and/or medical substance, and that said processing and analyzing equipment of the server is arranged to form a notification, if a cumulative amount of said nutrient and/or medical substance in a predetermined time period is either above or below an individualized intake limit defined for the user of said nutrient and/or medical substance.

12. The system according to claim 9, wherein the processing and analyzing equipment of the server is arranged to compare cumulative substance amounts of the nutrients and/or medical substances consumed by the user within a selected time period to intake limits set for said nutrients and/or medical substances, to select at least one nutrient or medical substance, the cumulative amount of which in said time period is below the defined intake limit, and if a value of the numerical probability weighting coefficient for said substance influencing a certain health property in the healing manner is above the preset limit, to communicate a proposal to the user's data terminal via said data transmission connection of said server of said nutrient and/or medical substance to be consumed by said user.

13. The system according to claim 9, wherein the system is configured to deliver the information to the data transmission connection of said server via at least one of a mobile station, PDA device, smart card, magnetic card, Internet browser, or digital television.

14. A non-transitory computer readable medium for offering proposals and/or information about suitability of nutrients, and/or medical substances for a user by communicating via a user's data terminal, the non-transitory computer readable medium being configured so that data transmission connections are established between a central server and data communication network and said user's data terminal, where said data communication network comprises information about relations between genes and health properties, how the genes influence said health properties, information about relations between nutrients and/or medical substances health properties and how the nutrients and/or medical substances influence said health properties, the non-transitory computer readable medium being configured to:

1)
   a) to gather via said data transmission connection from said data communication network continuously information of an influence of at least one gene and/or at least one gene being in a functional state to at least one health property in a healing or harmful manner with a certain probability, providing cross references between said genes and related health property and providing numerical probability weighting coefficient of the influence of at least one gene and/or at least one gene being in a functional state to at least one health property in a healing or harmful manner with a certain probability, b) data transmission connection from said data communication network continuously information of influences of nutrients and/or medical substances to at least one health property in a healing or harmful manner with a certain probability, providing cross references between said nutrients and/or medical substances and related health properties and providing numerical probability weighting coefficients to nutrients and/or medical substances influencing said health property in the healing or harmful manner with the certain probability, c) to gather via said data transmission connection information of user's gene and/or user's gene being in the functional state, and providing a numerical indication communicated by the data equipment in a predefined format of the user's gene and/or user's gene being in the functional state to identify said gene, and d) to gather via said data transmission connection from said user's data terminal information, or information pertaining to amounts, about nutrients and/or medical substances consumed and/or to be consumed by the user via an interactive graphical plate displayed by the user's data terminal;

whereupon the non-transitory computer readable medium is configured to perform next the following:

2) to compare by a processing and analyzing equipment of the server indicated user's gene with gene information gathered in step 1a) to find out correspondence;

3) to find by the processing and analyzing equipment of the server health properties related to said correspondence gene via the cross references provided in item 1a);

4) to select by the processing and analyzing equipment of the server the numerical probability weighting coefficient between said gene and at least one health property, to which said gene influences when being in the normal and/or in the functional state;

5) to find by a processing and analyzing equipment of the server nutrients and/or medical substances related to said health property via the cross references provided in item 1b);

6) to select by the processing and analyzing equipment of the server the numerical probability weighting coefficients between said health property of item 4) and nutrients and/or medical substances of item 5) influencing the said health property in the healing or harmful manner with the certain probability;

7) to find by a processing and analyzing equipment of the server information about nutrients and/or medical substances consumed and/or to be consumed by the user gathered in item 1d) and taking into account amounts of the corresponding nutrients and/or medical substances by adding or subtracting their amounts from the recommended amounts;

8) to form individualized optimal nutrition and/or medical substance information with amounts to be consumed by ordering by the processing and analyzing equipment of the server the numerical probability weighting coefficients determined in step 6) to describe the suitability of nutrients and/or medical substances for the user so that the nutrient and/or medical substance influencing to said health property in the most healing manner is offered as the proposal; and 9) to modify the amounts of the individualised optimal nutrition and/or medical substance provided in item 8) by adding or subtracting the already consumed amounts of corresponding nutrients and/or medical substances find out in item 7; and 10) to communicate via said data transmission connection the information about the nutrition and/or medical substance in the order provided in item 8) and with modified amounts provided in item 9) as a proposal to the user via the user's data terminal at least partly as an interactive graphical plate displayed by the user's data terminal information, when said non-transitory computer readable medium is ran at the server.

\* \* \* \* \*